United States Patent [19]
Guzaev et al.

[11] Patent Number: 6,121,437
[45] Date of Patent: Sep. 19, 2000

[54] PHOSPHATE AND THIOPHOSPHATE PROTECTING GROUPS

[75] Inventors: Andrei P. Guzaev; Muthiah Manoharan, both of Carlsbad, Calif.

[73] Assignee: Isis Pharmaceuticals, Inc., Carlsbad, Calif.

[21] Appl. No.: 09/268,797

[22] Filed: Mar. 16, 1999

[51] Int. Cl.$^7$ ............................ C07H 19/04; C07H 1/00
[52] U.S. Cl. ................... 536/26.1; 536/1.11; 536/4.1; 536/25.4; 536/25.31
[58] Field of Search ............................ 536/26.1, 1.11, 536/4.1, 25.4, 25.31

[56] References Cited

U.S. PATENT DOCUMENTS

| | | | |
|---|---|---|---|
| Re. 34,069 | 9/1992 | Köster et al. | 536/27 |
| 3,687,808 | 8/1972 | Merigan et al. | 195/28 |
| 4,415,732 | 11/1983 | Caruthers et al. | 536/27 |
| 4,458,066 | 7/1984 | Caruthers et al. | 536/27 |
| 4,500,707 | 2/1985 | Caruthers et al. | 536/27 |
| 4,668,777 | 5/1987 | Caruthers et al. | 536/27 |
| 4,725,677 | 2/1988 | Köster et al. | 536/27 |
| 4,973,679 | 11/1990 | Caruthers et al. | 536/27 |
| 5,026,838 | 6/1991 | Nojiri et al. | 536/27 |
| 5,132,418 | 7/1992 | Caruthers et al. | 536/27 |
| 5,149,798 | 9/1992 | Agrawal et al. | 536/27 |
| 5,210,264 | 5/1993 | Yau | 538/167 |
| 5,212,295 | 5/1993 | Cook | 536/26.7 |
| 5,212,304 | 5/1993 | Fung et al. | 536/26.1 |
| 5,670,633 | 9/1997 | Cook et al. | 536/23.1 |
| 5,705,621 | 1/1998 | Ravikumar | 536/26.1 |
| 5,734,041 | 3/1998 | Just et al. | 536/25.31 |
| 5,750,666 | 5/1998 | Caruthers et al. | 536/26.1 |

FOREIGN PATENT DOCUMENTS

| | | |
|---|---|---|
| 0 506 242 A1 | 3/1992 | European Pat. Off. . |
| WO 96/39413 | 12/1996 | WIPO . |

OTHER PUBLICATIONS

Alul, R.H. et al., "Oxalyl–CPG: a labile support for synthesis of sensitive oligonucleotide derivatives", *Nucl. Acid Res.*, 1991, 19, 1527–1532.

Bannwarth, W., "Synthesis of Oligodeoxynucleotides by the Phosphite–Triester Method Using Dimer Units and Different Phosphorous–Protecting Groups", *Helvetica Chim. Acta*, 1985, 68, 1907–1913.

Beaucage, S.L. et al., "Advances in the Synthesis of Oligonucleotides by the Phosphoramidite Approach", *Tetrahedron*, 1992, 48, 2223–2311.

Bielinska, A. et al., "Regulation of Gene Expression with Double–Stranded Phosphorothioate Oligonucleotides", *Science*, 1990, 250, 997–1000.

Brown, T. et al., "Modern machine–aided methods of oligodeoxyribonucleotide synthesis", *Oligonucleotides and Analogs A Practical Approach*, 1991, Chapter 1, Eckstein, F., ed., IRL Press, Oxford, 1–24.

Cook, P.D., "Medicinal Chemistry of Antisense Oligonucleotides—future opportunities", *Anti–Cancer Drug Design*, 1991, 6, 585–607.

Crooke, S.T. et al., "Pharmacokinetic Properties of Several Novel Oligonucleotide Analogs in mice", *J. Pharmacol. Exp. Therapeutics*, 1996, 277, 923–937.

Delgado, C. et al., "The Uses and Properties of PEG–Linked Proteins", *Crit. Rev. in Therapeutic Drug Carrier Sys.*, 1992, 9, 249–304.

Efimov, V.A. et al., "New efficient sulfurizing reagents for the preparation of oligodeoxyribonucleotide phosphorothioate analogues", *Nucl. Acids Res.*, 1995, 23, 4029–4033.

Englisch, U. et al., "Chemically Modified Oligonucleotides as Probes and Inhibitors", *Angew. Chem. Int. Ed. Eng.*, 1991, 30, 613–629.

Hamm, M.L. et al., "Incorporation of 2'-Deoxy-2'-mercaptocytidine into Oligonucleotides via Phosphoramidite Chemistry," *J. Org. Chem.*, 1997, 62, 3415–3420.

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent",*J. Org. Chem.*, 1990, 55, 4693–4699.

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Iyer et al., "Solid–Phase Stereoselective Synthesis of Oligonucleoside Phosphorothioates: The Nucleoside Bicyclic Oxazaphospholidines as Novel Synthons," *Tetra. Lett.*, 1998, 39, 2491–2494.

Kabanov, A.V., "A new class of antivrials: antisense olgonucleotides combined with a hydrophobic substituent effectively inhibit influenza virus reproduction and synthesis of virus–specific proteins in MDCK cells", *FEBS Letts.*, 1990, 259, 327–330.

Kamer, P.C.J. et al., "An Efficient Approach Toward the Synthesis of Phosphorothioate Diesters via the Schonberg Reaction", *Tetrahedron Letts.*, 1989, 30, 6757–6760.

Khorana, H. G. et al., "Studies on Polynucleotides: Total Synthesis of the Structural Gene for an Alanine Transfer Ribonucleic Acid from Yeast," *J. Mol. Biol.*, 1972, 72, 209–217.

Kroschwitz, J.I., "Polynucleotides", *Concise Encyclopedia of Polymer Science and Engineering*, 1990, John Wiley & Sons, New York, 858–859.

Kumar, G. et al., "Improvements in Oligodeoxyribonucleotide Synthesis: Methyl N,N–Dialkylphosphoramidite Dimer Units for Solid Support Phosphite Methodology", *J. Org. Chem.*, 1984, 49, 4905–4912.

(List continued on next page.)

*Primary Examiner*—Louise N. Leary
*Attorney, Agent, or Firm*—Woodcock Washburn Kurtz Mackiewicz & Norris LLP

[57] ABSTRACT

Novel phosphorus protecting groups, intermediates thereof, and synthetic processes for making the same are disclosed. Oligomeric compounds are prepared through the protection of one or more internucleosidic phosphorus functionalities, preferably followed by oxidation and cleavage of the protecting groups to provide oligonucleotides.

61 Claims, No Drawings

OTHER PUBLICATIONS

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Manoharan, M. et al., "Lipidic Nucleic Acids", *Tetrahedron Letts.*, 1995, 36, 3651–3654.

Manoharan M. et al., "Cholic Acid–Oligonucliotide Conjugates for Antisense Applications", *Bioorganic Med. Chem. Letts.*, 1994, 4, 1053–1060.

Manoharan, M. et al., "Chemical Modifications to Improve Uptake and Bioavailability of Antisense Oligonucleotides", *Annals NY Acad. Sciences*, 1992, 660, 306–309.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan M. et al., "Oligonucleotide Conjugates: Alteration of the Pharmacokinetic Properties of Antisense Agents", *Nucleosides and Nucleotides*, 1995, 14, 969–973.

Mishra, R.K. et al., "Improved leishmanicidal effect of phosphorotioate antisense oligonucleotides by LDL–medicated delivery", *Biochim. Et Biophysica*, 1995, 1264, 229–237.

Miura, K. et al., "Blockwise Mechanical Synthesis of Oligonucleotides by the Phosphoramidite Method", *Chem. Pharm. Bull.*, 1987, 35, 833–836.

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Polushin, N. N. et al., "Synthesis of Oligonucleotides Containing 2'–Azido–and 2'–Amino–2'–deoxyuridine Using Phosphotriester Chemistry," *Tetrahedron Letts.*, 1996, 37(19), 3227–3230.

Rao, M.V. et al., "Dibenzoyl Tetrasulphide–A Rapid Sulphur Transfer Agent in the Synthesis of Phosphorothioate Analogues of Oligonucleotides", *Tetrahedron Letts.*, 1992, 33, 4839–4842.

Ravasio, N. et al., "Selective Hydrogenations Promoted by Copper Catalysts, 1. Chemoselectivity, Regioselectivity, and stereoselectivity in the Hydrogenation of 3–Substituted Steroids", *J. Org. Chem.*, 1991, 56, 4329–4333.

Reese, C. B. et al., "The Chemical Synthesis of Oligo–and Poly–Nucleotides by the Phosphotriester Approach," *Tetrahedron*, 1978, 34, 3143–3179.

Saison–Behmoaras, T. et al., "Short modified antisense oligonucleotides directed against Ha–*ras* point mutation induce selective cleavage of the mRNA and inhibit T24 cells proliferation", *EMBO J.*, 1991, 10, 1111–1118.

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 273–288.

Secrist, J.A. et al., "Synthesis and Biological Activity of 4'–Thionucleosides", *10th International Roundtable: Nucleosides, Nucleotides and their Biological Applications*, Sep. 16–20, 1992, *Abstract 21,* Park City, Utah, 40.

Shea, R.G. et al., "Synthesis, hybridization properties and antiviral activity of lipid–oligodeoxynucletide conjugates", *Nucl. Acids Res.*, 1990, 18, 3777–3783.

Stec, W.J. et al., "Bis (O,O–Diisopropoxy Phosphinothioyl) Disulfide—A Highly Efficient Sulfurizing Reagent for Cost-–Effective Synthesis of Oligo(Nucleoside Phosphorothioate)s", *Tetrahedron Letts.*, 1993, 34, 5317–5320.

Stec, W.J. et al., "Novel route to oligo(deoxyribonucleoside phosphorothioates). Stereocontrolled synthesis of P–chiral oligo(deoxyribonucleoside phosphorothioates)", *Nucl. Acids Res.*, 1991, 19, 5883–5888.

Stec, W.J. et al., "Stereospecific Synthesis of P–chiral Analogs of oligonucleotides", *Methods in Molecular Biology*, 1993, vol. 20, Chapter 14, Humana Press, Totowa, NJ, 285–313.

Svinarchuk, F.P. et al., "Inhibition of HIV proliferation in MT–4 cells by antisense oligonucleotide conjugated to lipophilic groups", *Biochimie*, 1993, 79, 49–54.

Thomson, J. B. et al., "Synthesis and Properties of Diuridine Phosphate Analogues Containing Thio and Amino Modifications," *J. Org. Chem.*, 1996, 61, 6273–6281.

Vu, H. et al, "Internucleotide Phosphite Sulfurization with Tetraethylthiuram Disulfide. Phosphorothioate Oligonucleotide Synthesis via Phosphoramidite Chemistry", *Tetrahedron Letts.*, 1991, 32, 3005–3008.

Wilk et al., "Trifluoroacetylamino Alcohol as Phosphodiester Protecting Groups in the Synthesis of Oligodeoxyribonucleotides," *J. Org. Chem.*, 1997, 62, 6712–6713.

Wolter, A. et al., Polymer Support Oligonucleotide Synthesis XX: Synthesis of a Henhectacosa Deoxynucleotide by use of a Dimeric Phosphoramidite *Nucleosides & Nucleotides*, 1986, 5, 65–77.

Wright, P. et al., "Large Scale Synthesis of Oligonucleotides via phosphoramidite Nucleosides and a High–loaded Polystyrene Support", *Tetra. Letts.*, 1993, 34, 3373–3376.

Wu, H. et al., "Inhibition of in vitro transcription by specific double–stranded oligodeoxyribonucleotides", *Gene*, 1990, 89, 203–209.

Xu, Q. et al., "Use of 1,2,4–dithiazolidine (DtsNH) and 3–ethoxy–1,2,4–dithiazoline–5–one (EDITH) for synthesis of phosphorothioate–containing oligodeoxyribonucleotides", *Nucl. Acids Res.*, 1996, 24, 1602–1607.

Xu, Q. et al., "Efficient introduction of phosphorothioates into RNA oligonucleotides by 3–ethoxy–1,2, 4–dithiazoline–5–one (EDITH)", *Nucl. Acids Res.*, 1996, 24, 3634–3644.

Zioudrou et al., "The Participation of the Amide Group in the Solvolysis of Phosphoric Acid Eters. I. Phosphotriesters in Alkaline Media," *J. Am Chem. Soc.*, 1963, 85, 3258–3264.

96/39413

Agrawal, S. (ed.)., *Protocols for Oligonucleotides and Analogs,* Humana Press, Totowa, NJ, 1993.

Ausubel, F.M. et al., (eds.), *Current Protocols in Molecular Biology,* Current Publications, 1993.

Green and Wuts, *Protective Groups in Organic Synthesis,* 2d Ed., John Wiley & Sons, New York, Chapter 2, 1991.

Sambrook, J. et al. (eds.) *Molecular Cloning, A Laboratory Manual,* Second Ed., Cold Spring Harbor Laboratory Press, 1989.

U.S. application No. 08/398,901 filed Mar. 6,1995, Cook et al.

U.S. appliction No. 09/123,108 filed Jul. 27,1998, Manoharan et al.

PHOSPHATE AND THIOPHOSPHATE PROTECTING GROUPS

FIELD OF THE INVENTION

This invention relates generally to novel compounds which serve as protectors of internucleosidic phosphate and thiophiosphate functionalities during oligonucleotide synthesis.

BACKGROUND OF THE INVENTION

Oligonucleotides and their analogs have been developed and used in molecular biology in a variety of procedures as probes, primers, linkers, adapters, and gene fragments. The widespread use of such oligonucleotides has increased the demand for rapid, inexpensive and efficient procedures for their modification and synthesis. Early synthetic approaches to oligonucleotide synthesis included phosphodiester and phosphotriester chemistries. Khorana et al., *J. Molec. Biol.* 72, 209, 1972; Reese, *Tetrahedron Lett.* 34, 3143–3179, 1978. These approaches eventually gave way to more efficient modern methods, such as the use of phosphoramidite and H-phosphonate. Beaucage and Caruthers, *Tetrahedron Lett.*, 22, 1859–1862, 1981; Agrawal and Zamecnik, U.S. Pat. No. 5,149,798, issued 1992.

Solid phase techniques continue to play a large role in oligonucleotidic synthetic approaches. Typically, the 3'-most nucleoside is anchored to a solid support which is functionalized with hydroxyl or amino residues. The additional nucleosides are subsequently added in a step-wise fashion to form the desired linkages between the 3'-functional group of the incoming nucleoside, and the 5'-hydroxyl group of the support bound nucleoside. Implicit to this step-wise assembly is the judicious choice of suitable phosphorus protecting groups. Such protecting groups serve to shield phosphorus moiety of the nucleoside base portion of the growing oligomer until such time that it is cleaved from the solid support. Consequently, new protecting groups, which are versatile in oligonucleotidic synthesis, are needed.

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Example 12s of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents. Other mechanisms of action have also been proposed.

Transcription factors interact with double-stranded DNA during regulation of transcription. Oligonucleotides can serve as competitive inhibitors of transcription factors to modulate their action. Several recent reports describe such interactions (see Bielinska, A., et. al., *Science,* 1990, 250, 997–1000; and Wu, H., et. al., *Gene,* 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual,* Second Ed., J. Sambrook, et al., Eds., Cold Spring Harbor Laboratory Press, 1989; and *Current Protocols In Molecular Biology,* F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual,* supra. See also "DNA-protein interactions and The Polymerase Chain Reaction" in Vol. 2 of *Current Protocols In Molecular Biology,* supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The chemical literature discloses numerous processes for coupling nucleosides through phosphorous-containing covalent linkages to produce oligonucleotides of defined sequence. One of the most popular processes is the phosphoramidite technique (see, e.g., Advances in the Synthesis of Oligonucleotides by the Phosphoramidite Approach, Beaucage, S. L.; Iyer, R. P., *Tetrahedron*, 1992, 48, 2223–2311 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

The phosphoramidite technique, however, has significant disadvantages. For example, cyanoethyl phosphoramidite monomers are quite expensive. Although considerable quantities of monomer go unreacted in a typical phosphoramidite coupling, unreacted monomer can be recovered, if at all, only with great difficulty.

The ability of the acylaminoethyl group to serve as a protecting group for certain phosphate diesters was first observed by Ziodrou and Schmir. Zioudrou et al., *J. Amer. Chem. Soc.*, 85, 3258, 1963. A version of this method was extended to the solid phase synthesis of oligonucleotide dimers, and oligomers with oxaphospholidine nucleoside building blocks as substitutes for conventional phosphoramidites. Iyer et al., *Tetrahedron Lett.*, 39, 2491–2494, 1998; PCT International Publication WO/9639413, published Dec. 12, 1996. Similar methods using N-trifluoroacetyl-aminoalkanols as phosphate protecting groups has also been reported by Wilk et al., *J. Org. Chem.*, 62, 6712–6713, 1997. This deprotection is governed by a mechanism that involves removal of N-trifluoroacetyl group followed by cyclization of aminoalkyl phosphotriesters to azacyclanes, which is accompanied by the release of the phosphodiester group.

SUMMARY OF THE INVENTION

It has been discovered that certain acylaminoalkyl, thioacylaminoalkyl, carbamoylalkyl and similar chemical groups are capable of serving as efficient protectors of various internucleosidic phosphate moieties during oligonucleotide synthesis. Advantageously, the protecting groups of the present invention can be removed under mild conditions without affecting the efficiency of the phosphoramidite coupling. Moreover, because removal of the acylaminoalkyl group leads to benign by-products, the artisan need not be concerned with toxic contaminants or undesired alkylation products.

The precursors of the protecting groups of the present invention are readily available which leads to cost reduction overall. N-benzoylaminoalkanols, N-thiobenzoylaminoalkanols, and (2-hydroxyethyl)N-arylcarbamates may be obtained, for example, from aminoalcohols and ethyleneglycols which are available in commercial abundance.

Several processes known to the skilled artisan for the solid phase synthesis of oligonucleotide compounds may be employed with the present invention. These are generally disclosed in the following U.S. Pat. Nos.: 4,458,066; issued Jul. 3, 1984; 4,500,707, issued Feb. 19, 1985; and 5,132,418, issued Jul. 21, 1992. Additionally, a process for the preparation of oligonucleotides using phosphoramidite intermediates is disclosed in U.S. Pat. No. 4,973,679, issued Nov. 27, 1990.

A process for the preparation of phosphoramidites is disclosed in U.S. Pat. No. 4,415,732, issued Nov. 15, 1983. Phosphoramidite nucleoside compounds are disclosed in U.S. Pat. No. 4,668,777, issued May 26, 1987. A process for the preparation of oligonucleotides using a β-eliminating phosphorus protecting group is disclosed in U.S. Pat. No. Re. 34,069, issued Sep. 15, 1992. A process for the preparation of oligonucleotides using a β-eliminating or allylic phosphorus protecting group is disclosed in U.S. Pat. No. 5,026,838, issued Jun. 25, 1991. All of the foregoing may benefit from the present invention.

It is an object of the present invention to provide novel compounds of Formula I:

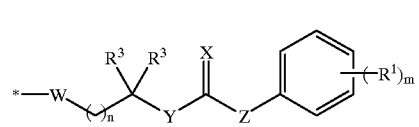

which may serve as phosphorus protecting groups; wherein * indicates the point of attachment to the phosphorus of an oligomeric compound, and $R^1$, $R^3$, X, Y, Z, n, and m are defined below.

It is a further object of the present invention to provide methods for the preparation of oligomeric compounds having phosphorus-containing functionalities, employing the protecting groups of Formula I.

It is a further object of the present invention to provide synthetic intermediates useful in such methods. Other objects will be apparent to those skilled in the art.

These objects are satisfied by the present invention which provides novel phosphorus protecting groups, methods for making compounds employing such protecting groups, and intermediates thereof.

DETAILED DESCRIPTION OF THE PREFERRED EMBODIMENTS

In a first embodiment, the present invention provides a method for the preparation of an oligomeric compound comprising a moiety of Formula X:

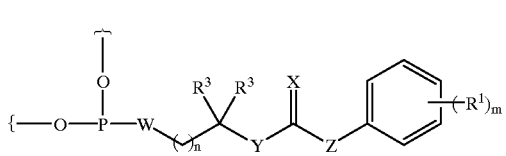

wherein:
W is selected independently from O and S;
X is selected independently from O and S;
Y is selected independently from O and $NR^2$;
Z is selected independently from a single bond, O, and $NR^2$;
$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl;

alternatively, two $R^1$ groups, when on adjacent carbons of the phenyl ring, join to form a napthyl ring that includes said phenyl ring;

$R^2$, at each occurrence, is selected independently from H, $C_{1-6}$ alkyl, $C_{2-6}$ alkenyl, $C_{2-6}$ alkynyl, $C_{3-6}$ cycloalkyl, and phenyl;

$R^3$, at each occurrence, is selected independently from hydrogen, $C_{1-6}$ alkyl, $C_{2-6}$ alkenyl, $C_{2-6}$ alkynyl, $C_{3-6}$ cycloalkyl, and phenyl;

$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;

n is selected independently from 0, 1, 2, and 3; and m is selected independently from 0, 1, 2, and 3;

the method comprising:

(a) providing a compound of Formula II:

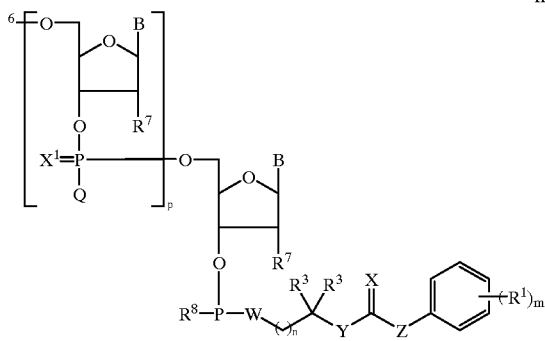

II wherein:

$R^6$, at each occurrence, is selected independently from H, a hydroxyl protecting group, and a linker connected to a solid support;

$R^7$, at each occurrence, is indepedently H, hydroxyl, $C_{1-20}$ alkyl, $C_{3-20}$ alkenyl, $C_{2-20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, dilulfide, silyl, aryl, heterocycle, carbocycle, intercalator, reporter molecule, conjugate, polyamine, polyamide, polyalkylene glycol, polyether, or one of formula XII or XIII:

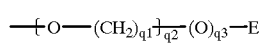

XII

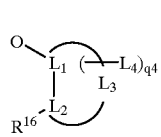

XIII wherein

E is selected from $C_{1-10}$ alkyl, $N(R^{15})(R^{17})$ and $N=C(R^{15})(R^{17})$;

$R^{15}$ and $R^{17}$ are independently selected from H, $C_{1-10}$ alkyl, dialkylaminoalkyl, a nitrogen protecting group, a tethered or untethered conjugate group, a linker to a solid support, or alternatively $R^{15}$ and $R^{17}$, together, are joined in a nitrogen protecting group or a ring structure that can include at least one additional heteroatom selected from N and O;

$q^1$ is from 1 to 10;

$q^2$ is from 1 to 10;

$q^3$ is 0 or 1;

$R^{16}$ is $OR^{18}$, $SR^{18}$, or $N(R^{18})_2$;

$R^{18}$ is selected independently from H, $C_1-C_8$ alkyl, $C_1-C_8$ haloalkyl, $C(=NH)N(H)R^{19}$, $C(=O)N(H)R^{19}$ and $OC(=O)N(H)R^{19}$;

$R^{19}$ is H or $C_1-C_8$ alkyl;

$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$L_4$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R^{15})(R^{17})$ $OR^{15}$, halo, $SR^{15}$ or CN; and $q^4$ is, 0, 1 or 2;

$R^8$ is selected independently from $NR^{8a}R^{8b}$, and a 5–6 membered heterocyclic system containing 1–4 heteroatoms selected independently from N, O, and S;

$R^{8a}$ and $R^{8b}$, at each occurrence, are selected independently from $C_{1-10}$ alkyl and $C_{3-7}$ cycloalkyl;

$X^1$ is selected independently from O and S;

B, at each occurrence, is independently selected from a protected or unprotected naturally occurring nucleobase, and a protected or unprotected non-naturally occurring nucleobase;

q is selected independently from 1, 2, 3, 4, 5, 6, 7, 8, 9, and 10;

p is an integer selected independently from 0 to about 50;

Q, at each occurrence, is selected independently from OH, SH, and

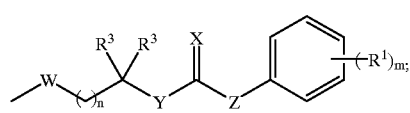

(b) reacting the compound of Formula II with a compound of Formula III:

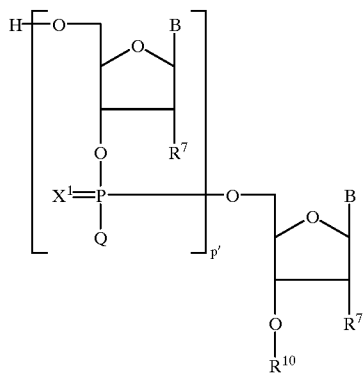

wherein $R^{10}$ is selected independently from a hydroxyl protecting group, and a linker connected to a solid support;

with the proviso that $R^6$ and $R^{10}$ are not both simultaneously a linker connected to a solid support; and p' is an integer selected independently from 0 to about 50;

to form the oligomeric compound.

In another embodiment, the method further comprises treating said oligomeric compound with a reagent under conditions of time temperature and pressure effective to oxidize or sulfurize the oligomeric compound.

In a preferred embodiment, $R^{10}$ is a linker connected to a solid support, further comprising treating the oligomeric compound with a reagent under conditions of time temperature and pressure effective to deprotect the oligomeric compound. In another preferred embodiment, the deprotection is effective to remove the oligomeric compound from the solid support. In another preferred embodiment, the method further comprises treating the oligomeric compound with a reagent under conditions of time temperature and pressure effective to remove the oligomeric compound from the solid support.

In another preferred embodiment, $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$; $R^2$ is selected independently from H and $C_{1-3}$ alkyl; $R^3$ is H; Y is N—$R^2$; Z is said bond; n is 1; and m is 1. In a more preferred embodiment, $R^1$ is $OCH_3$, and is in the para position. In other more preferred embodiments, W and $X^1$ are either sulfur or oxygen. In an even more preferred embodiment, each $R^{8a}$ and $R^{8b}$ are isopropyl.

In another embodiment, in the preparation of an oligomeric compound comprising a moiety of Formula X, the compound of Formula II is obtained by reaction of a compound having Formula V:

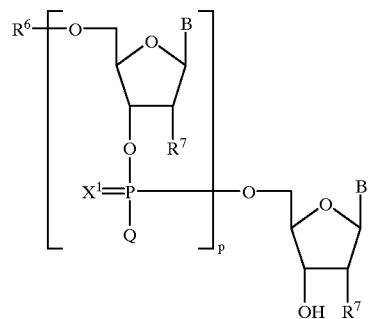

with a compound of Formula VI:

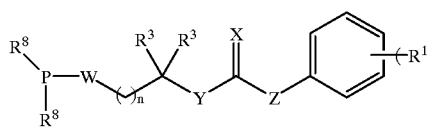

in the presence of an acid. In another embodiment, in the preparation of an oligomeric compound comprising a moiety of Formula X, the compound of Formula II is obtained by reaction of a compound of Formula V:

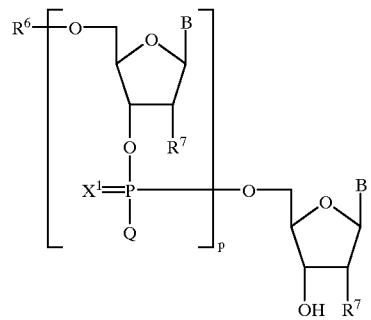

with a chlorophosphine compound of formula ClP$(NR^{8a}R^{8b})_2$, followed by reaction with a compound of Formula I-i:

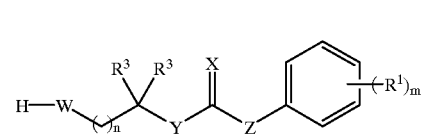

in the presence of an acid.

In a preferred embodiment of the preparation of the compound of forumula II, W is O; Z is selected independently from a single bond and $NR^2$; $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$; $R^3$ is selected independently from H and $CH_3$; $R^4$ are H; n is selected independently from 1 and 2; and m is 1.

In another embodiment, the present invention provides a method for the preparation of a compound of Formula II:

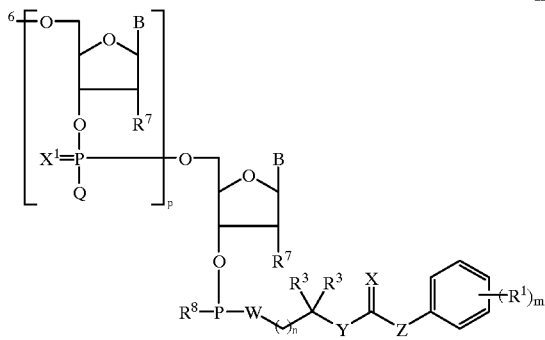

wherein:

W is selected independently from O and S;

X is selected independently from O and S;

Y is selected independently from O and NR$^2$;

Z is selected independently from a single bond, O, and NR$^2$;

R$^1$, at each occurrence, is selected independently from C$_{1-6}$ alkyl, C$_{2-6}$ alkenyl, C$_{2-6}$ alkynyl, C$_{3-6}$ cycloalkyl, CN, NO$_2$, Cl, Br, F, I, CF$_3$, OR$^4$, NR$^{5a}$R$^{5b}$, and phenyl;

alternatively, two R$^1$ groups, when on adjacent carbons of the phenyl ring, join to form a napthyl ring that includes said phenyl ring;

R$^2$, at each occurrence, is selected independently from H, C$_{1-6}$ alkyl, C$_{2-6}$ alkenyl, C$_{2-6}$ alkynyl, C$_{3-6}$ cycloalkyl, and phenyl;

R$^3$, at each occurrence, is selected independently from hydrogen, C$_{1-6}$ alkyl, C$_{2-6}$ alkenyl, C$_{2-6}$ alkynyl, C$_{3-6}$ cycloalkyl, and phenyl;

R$^4$ is selected independently from C$_{1-6}$ alkyl, C$_{3-6}$ cycloalkyl, and phenyl;

R$^{5a}$ and R$^{5b}$, at each occurrence, are selected independently from C$_{1-6}$ alkyl, C$_{3-6}$ cycloalkyl, and phenyl;

n is selected independently from 0, 1, 2, and 3; and m is selected independently from 0, 1, 2, and 3

R$^6$, at each occurrence, is selected independently from H, a hydroxyl protecting group, and a linker connected to a solid support;

R$^7$, at each occurrence, is indepedently H, hydroxyl, C$_1$–C$_{20}$ alkyl, C$_3$–C$_{20}$ alkenyl, C$_2$–C$_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, dilulfide, silyl, aryl, heterocycle, carbocycle, intercalator, reporter molecule, conjugate, polyamine, polyamide, polyalkylene glycol, polyether, or one of formula XII or XIII:

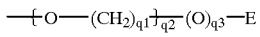 XII

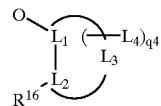 XIII wherein

E is selected from C$_1$–C$_{10}$ alkyl, N(R$^{15}$)(R$^{17}$) and N=C(R$^{15}$)(R$^{17}$);

R$^{15}$ and R$^{17}$ is independently selected from H, C$_1$–C$_{10}$ alkyl, dialkylaminoalkyl, a nitrogen protecting group, a tethered or untethered conjugate group, a linker to a solid support, or alternatively R$^{15}$ and R$^{17}$, together, are joined in a nitrogen protecting group or a ring structure that can include at least one additional heteroatom selected from N and O;

q$^1$ is from 1 to 10;

q$^2$ is from 1 to 10;

q$^3$ is 0 or 1;

R$^{16}$ is OR$^{18}$, SR$^{18}$, or N(R$^{18}$)$_2$;

R$^{18}$ is selected independently from H, C$_1$–C$_8$ alkyl, C$_1$–C$_8$ haloalkyl, C(=NH)N(H)R$^{19}$, C(=O)N(H)R$^{19}$ and OC(=O)N(H)R$^{19}$;

R$^{19}$ is H or C$_1$–C$_8$ alkyl;

L$_1$, L$_2$ and L$_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

L$_4$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$^{15}$)(R$^{17}$) OR$^{15}$, halo, SR$^{15}$ or CN; and q$^4$ is, 0, 1 or 2;

R$^8$ is selected independently from NR$^{8a}$R$^{8b}$, and a 5–6 membered heterocyclic system containing 1–4 heteroatoms selected independently from N, O, and S;

R$^{8a}$ and R$^{8b}$, at each occurrence, are selected independently from C$_{1-10}$ alkyl and C$_{3-7}$ cycloalkyl;

X$^1$ is selected independently from O and S;

B, at each occurrence, is independently selected from a protected or unprotected naturally occurring nucleobase, and a protected or unprotected non-naturally occurring nucleobase;

q is selected independently from 1, 2, 3, 4, 5, 6, 7, 8, 9, and 10;

p is an integer selected independently from 0 to about 50;

Q, at each occurrence, is selected independently from SH, OH, and

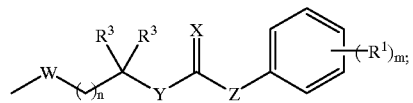

the method comprising:

reacting a nucleoside of Formula V:

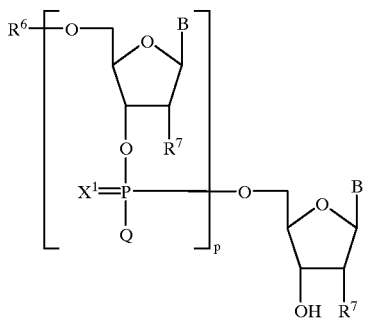

with a chlorophosphine compound of formula ClP—$(R^8)_2$, in the presence of a base; and protecting the product by reaction with a compound of Formula I-i:

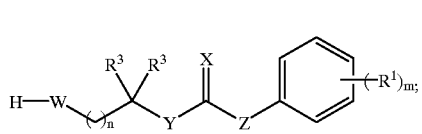

in the presence of an acid to form the compound of Formula II.

In a preferred embodiment, the present invention provides the product of this reaction. In another preferred embodiment, $R^1$ is in the meta or para position and is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$; $R^2$ is selected independently from $CH_3$, $CH_2CH_3$, and $CH(CH_3)_2$; $R^3$ is selected independently from H and $CH_3$; n is selected independently from 1 and 2; and m is 1. In a more preferred embodiment, W is O. In an even more preferred embodiment, $R^8$ is $NR^{8a}R^{8b}$, and $R^{8a}$ and $R^{8b}$ are each isopropyl. In another more preferred embodiment, p is 0.

In another embodiment, the present invention provides a compound of Formula I:

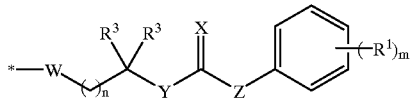

wherein:
* indicates the point of attachment to the phosphorus atom of an oligomeric compound;
W is selected independently from O and S;
X is selected independently from O and S;
Y is selected independently from O and $NR^2$;
Z is selected independently from a single bond, O, and $NR^2$;
$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl; alternatively, two $R^1$ groups, when on adjacent carbons of the phenyl ring, join to form a napthyl ring that includes said phenyl ring;

$R^2$, at each occurrence, is selected independently from H, $C_{1-6}$ alkyl, $C_{2-6}$ alkenyl, $C_{2-6}$ alkynyl, $C_{3-6}$ cycloalkyl, and phenyl;

$R^3$, at each occurrence, is selected independently from hydrogen, $C_{1-6}$ alkyl, $C_{2-6}$ alkenyl, $C_{2-6}$ alkynyl, $C_{3-6}$ cycloalkyl, and phenyl;

$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;

n is selected independently from 0 to about 3; and m is selected independently from 0 to about 3.

In a preferred embodiment, $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$. In another preferred embodiment, each $R^3$ is hydrogen, Y is $NR^2$, and Z is a single bond or $NR^2$. In a more preferred embodiment, $R^2$ is selected independently from H, $CH_3$, $CH_2CH_3$, and $CH(CH_3)_2$; n is selected independently from 1 and 2; and m is 1. In an even more preferred embodiment, $R^2$ is H; n is selected independently from 1 and 2; m is 1. In a even further more preferred embodiment, $R^1$ is $OCH_3$.

In another preferred embodiement, the present invention provides a compound of Formula VII:

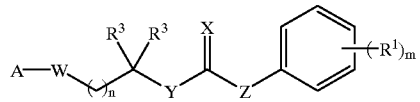

wherein:
W is selected independently from O and S;
X is selected independently from O and S;
Y is selected independently from O and $NR^2$;
Z is selected independently from a single bond, O, and $NR^2$;
$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl; alternatively, two $R^1$ groups, when on adjacent carbons of the phenyl ring, join to form a napthyl ring that includes said phenyl ring;

$R^2$, at each occurrence, is selected independently from H, $C_{1-6}$ alkyl, $C_{2-6}$ alkenyl, $C_{2-6}$ alkynyl, $C_{3-6}$ cycloalkyl and phenyl;

$R^3$, at each occurrence, is selected independently from hydrogen, $C_{1-6}$ alkyl, $C_{2-6}$ alkenyl, $C_{2-6}$ alkynyl, $C_{3-6}$ cycloalkyl, and phenyl;

$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;

n is selected independently from 0, 1, 2, and 3;

m is selected independently from 0, 1, 2, and 3;

A is selected independently from $(R^8)_2P$, $R^8R^{11}P$, $R^8R^{12}P$, and $R^{11}R^{12}P$;

$R^8$ is selected independently from $NR^{8a}R^{8b}$, and a 5–6 membered heterocyclic system containing 1–4 heteroatoms selected independently from N, O, and S;

$R^{8a}$ and $R^{8b}$, at each occurrence, are selected independently from $C_{1-10}$ alkyl and $C_{3-7}$ cycloalkyl;

$R^{11}$ is a compound of Formula VIII:

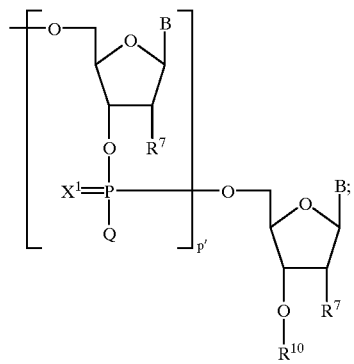

$R^7$, at each occurrence, is indepedently H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, dilulfide, silyl, aryl, heterocycle, carbocycle, intercalator, reporter molecule, conjugate, polyamine, polyamide, polyalkylene glycol, polyether, or one of formula XII or XIII:

$$\text{—}[\text{O}\text{—}(\text{CH}_2)_{q1}]_{q2}(\text{O})_{q3}\text{—E} \qquad \text{XII}$$

XIII

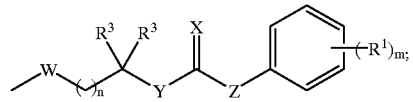

wherein

E is selected from $C_1$–$C_{10}$ alkyl, $N(R^{15})(R^{17})$ and $N=C(R^{15})(R^{17})$;

$R^{15}$ and $R^{17}$ is independently selected from H, $C_1$–$C_{10}$ alkyl, dialkylaminoalkyl, a nitrogen protecting group, a tethered or untethered conjugate group, a linker to a solid support, or alternatively $R^{15}$ and $R^{17}$, together, are joined in a nitrogen protecting group or a ring structure that can include at least one additional heteroatom selected from N and O;

$q^1$ is from 1 to 10;

$q^2$ is from 1 to 10;

$q^3$ is 0 or 1;

$R^{16}$ is $OR^{18}$, $SR^{18}$, or $N(R^{18})_2$;

$R^{18}$ is selected independently from H, $C_1$–$C_8$ alkyl, $C_1$–$C_8$ haloalkyl, $C(=NH)N(H)R^{19}$, $C(=O)N(H)R^{19}$ and $OC(=O)N(H)R^{19}$;

$R^{19}$ is H or $C_1$–$C_8$ alkyl;

$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$L_4$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R^{15})(R^{17})$, $OR^{15}$, halo, $SR^{15}$ or CN; and $q^4$ is, 0, 1 or 2;

$X^1$ is selected independently from O and S;

B, at each occurrence, is independently selected from a protected or unprotected naturally occurring nucleobase, and a protected or unprotected non-naturally occurring nucleobase;

$R^{10}$ is selected independently from H, a hydroxyl protecting group, and a linker connected to a solid support;

p' is an integer selected independently from 0 to about 50;

Q, at each occurrence, is selected independently from SH, OH and

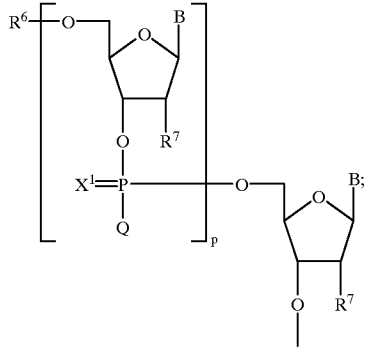

$R^{12}$ is a compound of Formula IX:

IX

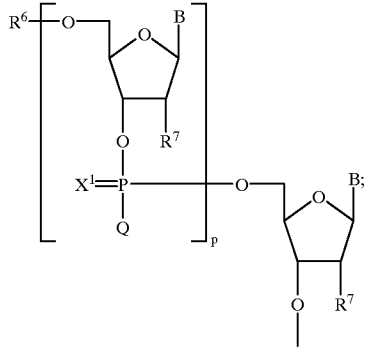

wherein:

$R^6$ is selected independently from H, a hydroxyl protecting group, and a linker connected to a solid support; and p is an integer selected independently from 0 to about 50;

with the provisos that the sum of p and p' does not exceed 50, and when A is $PR^{11}R^{12}$, $R^6$ and $R^{10}$ are not both simultaneously a linker connected to a solid support.

In a preferred embodiment, m is 1, and $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$. In another preferred embodiment, $R^3$ is hydrogen, Y is $NR^2$, and Z a single bond or $NR^2$. In other preferred embodiments, W is consistently O or S.

In another preferred embodiment, A is $P(R^8)_2$. In a more preferred embodiment, $R^8$ is $N(CH(CH_3)_2)_2$. In another preferred embodiment, A is $PR^{12}R^8$. In a more preferred embodiment, p is 0. In another more preferred embodiment, $R^6$ is a hydroxyl protecting group. In an even more preferred embodiment, Y is $NR^2$, $R^2$ is selected independently from H, $CH_3$, $CH_2CH_3$, and $CH(CH_3)_2$; n is selected independently from 1 and 2; m is 1, and $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$. In another preferred embodiment, A is $PR^{11}R^8$.

In another preferred embodiment, the compound of Formula VII is:

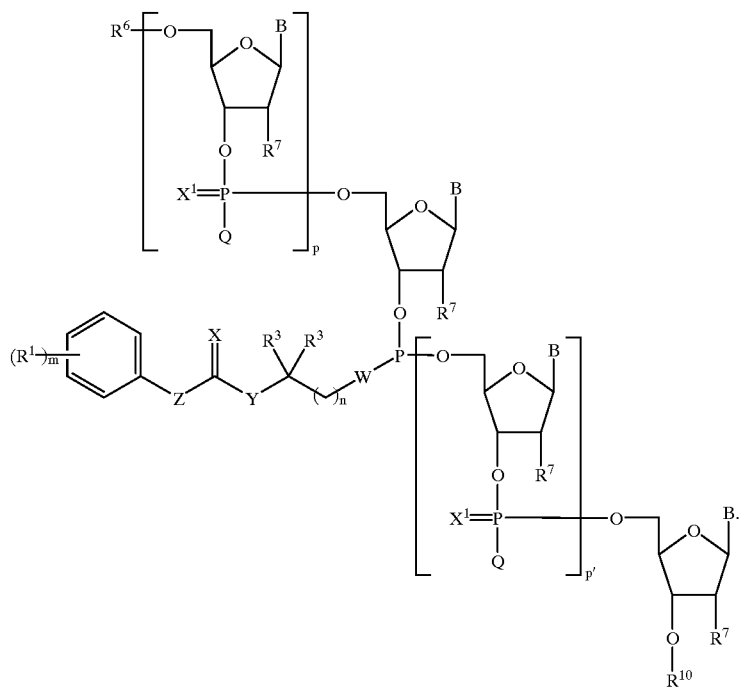

VII

In a more preferred embodiment, Y is $NR^2$; $R^2$ is selected independently from H, $CH_3$, $CH_2CH_3$, and $CH(CH_3)_2$; n is selected independently from 1 and 2; and m is 1. In another more preferred embodiment, $R^{10}$ is a linker connected to a solid support. In another more preferred embodiment, $R^{10}$ is H. In another more preferred embodiment, p and p' are 0.

In another embodiment, the present invention provides a compound of Formula XI:

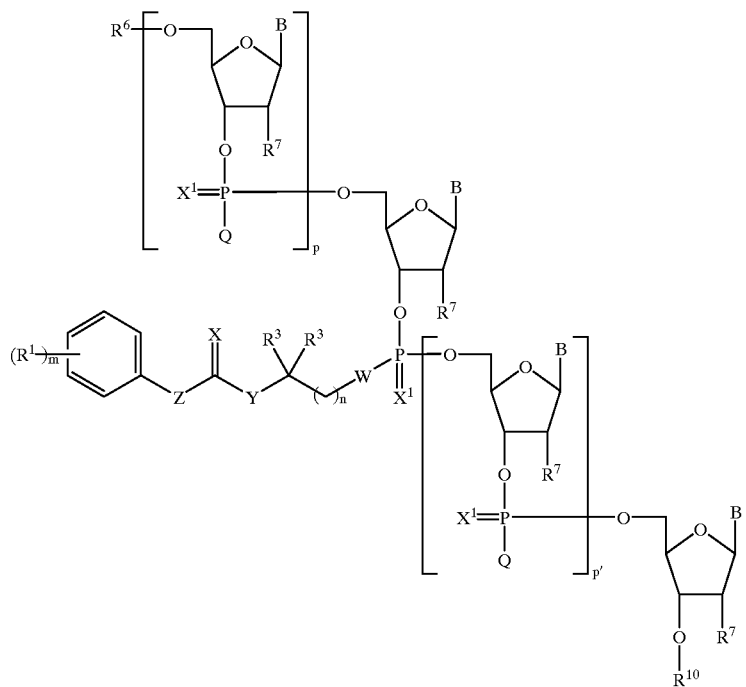

XI wherein:

W is selected independently from O and S;

X is selected independently from O and S;

Y is selected independently from O and $NR^2$;

Z is selected independently from a single bond, O, and $NR^2$;

$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl;

alternatively, two $R^1$ groups, when on adjacent carbons of the phenyl ring, join to form a napthyl ring that includes said phenyl ring;

$R^2$, at each occurrence, is selected independently from H, $C_{1-6}$ alkyl, $C_{2-6}$ alkenyl, $C_{2-6}$ alkynyl, $C_{3-6}$ cycloalkyl, and phenyl;

$R^3$, at each occurrence, is selected independently independently from hydrogen, $C_{1-6}$ alkyl, $C_{2-6}$ alkenyl, $C_{2-6}$ alkynyl, $C_{3-6}$ cycloalkyl, and phenyl;

$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;

$R^6$ is selected independently from H, a hydroxyl protecting group, and a linker connected to a solid support;

$R^7$, at each occurrence, is indepedently H, hydroxyl, $C_1-C_{20}$ alkyl, $C_3-C_{20}$ alkenyl, $C_2-C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, dilulfide, silyl, aryl, heterocycle, carbocycle, intercalator, reporter molecule, conjugate, polyamine, polyamide, polyalkylene glycol, polyether, or one of formula XII or XIII:

$$-\!\!\!+\!\!O-\!\!(CH_2)_{q1}\!\!+_{q2}\!\!(O)_{q3}-\!E \qquad \text{XII}$$

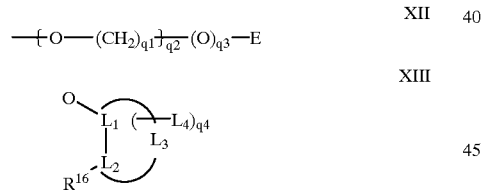

XIII wherein

E is selected from $C_1-C_{10}$ alkyl, N $(R^{15})(R^{17})$ and N=C $(R^{15})(R^{17})$;

$R^{15}$ and $R^{17}$ is independently selected from H, $C_1-C_{10}$ alkyl, dialkylaminoalkyl, a nitrogen protecting group, a tethered or untethered conjugate group, a linker to a solid support, or alternatively $R^{15}$ and $R^{17}$, together, are joined in a nitrogen protecting group or a ring structure that can include at least one additional heteroatom selected from N and O;

$q^1$ is from 1 to 10;

$q^2$ is from 1 to 10;

$q^3$ is 0 or 1;

$R^{16}$ is $OR^{18}$, $SR^{18}$, or $N(R^{18})_2$;

$R^{18}$ is selected independently from H, $C_1-C_8$ alkyl, $C_1-C_8$ haloalkyl, $C(=NH)N(H)R^{19}$, $C(=O)N(H)R^{19}$ and $OC(=O)N(H)R^{19}$;

$R^{19}$ is H or $C_1-C_8$ alkyl;

$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$L_4$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R^{15})(R^{17})$ $OR^{15}$, halo, $SR^{15}$ or CN; and $q^4$ is, 0, 1 or 2;

$R_8$ is selected independently from $NR^{8a}R^{8b}$, and a 5–6 membered heterocyclic system containing 1–4 heteroatoms selected independently from N, O, and S;

$R^{8a}$ and $R^{8b}$, at each occurrence, are selected independently from $C_{1-10}$ alkyl and $C_{3-7}$ cycloalkyl;

n is selected independently from 0, 1, 2, and 3;

m is selected independently from 0, 1, 2, and 3;

$X^1$ is selected independently from O and S;

B, at each occurrence, is independently selected independently from a protected or unprotected naturally occurring nucleobase, and a protected or unprotected non-naturally occurring nucleobase;

$R^{10}$ is selected independently from H, a hydroxyl protecting group, and a linker connected to a solid support;

Q, at each occurrence, is selected independently from SH, OH, and

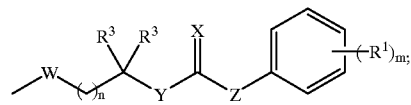

p' is an integer selected independently from 0 to about 50;

p is an integer selected independently from 0 to about 50;

with the provisos that the sum of p and p' does not exceed 50, and $R^6$ and $R^{10}$ are not both simultaneously a linker connected to a solid support.

In a preferred embodiment, $R^{10}$ is a linker connected to a solid support. In another preferred embodiment, $R^{10}$ is H. In a more preferred embodiment, $R^3$ is selected independently from H and $CH_3$; n is selected independently from 1 and 2; m is 1; $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$; and W is O. In another preferred embodiment, W is o. In a preferred embodiment, each Q has the formula:

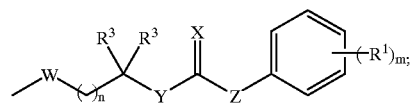

and p is an integer selected independently from 2 to 50.

In a another embodiment, the present invention provides a compound of Formula VI:

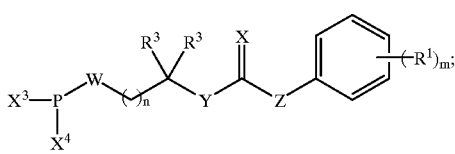

VI wherein:

W is selected independently from O and S;

X is selected independently from O and S;

Y is selected independently from O and $NR^2$;

Z is selected independently from a single bond, O, and $NR^2$;

$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl; alternatively, two $R^1$ groups, when on adjacent carbons of the phenyl ring, join to form a napthyl ring that includes said phenyl ring;

$R^2$, at each occurrence, is selected independently from H, $C_{1-6}$ alkyl, $C_{2-6}$ alkenyl, $C_{2-6}$ alkynyl, $C_{3-6}$ cycloalkyl, and phenyl;

$R^3$, at each occurrence, is selected independently from hydrogen, $C_{1-6}$ alkyl, $C_{2-6}$ alkenyl, $C_{2-6}$ alkynyl, $C_{3-6}$ cycloalkyl, and phenyl;

$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;

n is selected independently from 0, 1, 2, and 3;

m is selected independently from 0, 1, 2, and 3.

$X^3$ is selected independently from Br, Cl, and I; and $X^4$ is selected independently from $NR^aR^b$, and a 5–6 membered heterocyclic system containing 1–4 heteroatoms selected from N, O, and S;

$R^a$ and $R^b$, at each occurrence, are selected independently from $C_{1-10}$ alkyl and $C_{3-7}$ cycloalkyl.

In a preferred embodiment, $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, N $(CH_2CH_3)_2$, and $N(CH(CH_3)_2)_2$; $R^2$ is selected independently from H, $CH_3$, $CH_2CH_3$, and $CH(CH_3)_2$; $R^3$ is selected independently from H and $CH_3$; n is selected independently from 1 and 2; and m is 1, and $X^3$ is Cl.

In another embodiment, the present invention provides the foregoing embodiments, wherein $R^3$ is H, Y is $NR^2$, $R^2$ is $CH(CH_3)_2$, X is O, Z is a single bond, n is 1, m is 1, and $R^1$ is $OCH_3$ and is in the para position.

DEFINITIONS

The reactions of the synthetic methods claimed herein are carried out in suitable solvents which may be readily understood by one of skill in the art of organic synthesis, the suitable solvents generally being any solvent which is substantially nonreactive with the starting materials (reactants), the intermediates, or products at the temperatures at which the reactions are carried out, i.e., temperatures may range from the solvent's freezing temperature to the solvent's boiling temperature. A given reaction may be carried out in one solvent or a mixture of more than one solvent. Depending on the particular reaction step, suitable solvents for a particular reaction step may be selected.

The compounds described herein may have asymmetric centers. Unless otherwise indicated, all chiral, diastereomeric, and racemic forms are included in the present invention. Geometric isomers may also be present in the compounds described herein, and all such stable isomers are contemplated by the present invention. It will be appreciated that compounds of the present invention that contain asymmetrically substituted carbon atoms may be isolated in optically active or racemic forms or by synthesis.

The present invention includes all isotopes of atoms occurring in the intermediates or final compounds. Isotopes include those atoms having the same atomic number but different mass numbers. By way of example, and without limitation, isotopes of hydrogen include tritium and deuterium.

The methods of the present invention are useful for the preparation of all compounds containing phosphorus functionalities. As used herein, functionality includes, but is not limited to phosphite, phosphodiester, phosphorothioate, and/or phosphorodithioate residues, and oligomeric compounds containing monomeric subunits that are joined by a variety of functionality linkages, including phosphite, phosphodiester, phosphorothioate, and/or phosphorodithioate linkages.

As used herein, "oligomeric compound" refers to compounds containing a plurality of monomeric subunits that are joined by phosphorus-containing linkages, such as phosphite, phosphodiester, phosphorothioate, and/or phosphorodithioate linkages. Oligomeric compounds therefore include oligonucleotides, their analogs, and synthetic oligonucleotides. In preferred embodiments, the methods of the invention are used for the preparation of oligonucleotides and their analogs.

As used herein, the term "oligonuclotide analog" means compounds that can contain both naturally occurring (i.e. "natural") and non-naturally occurring synthetic moieties, for example, nucleosidic subunits containing modified sugar and/or nucleobase portions. Such oligonucleotide analogs are typically structurally distinguishable from, yet functionally interchangeable with, naturally occurring or synthetic wild type oligonucleotides. Thus, oligonucleotide analogs include all such structures which function effectively to mimic the structure and/or function of a desired RNA or DNA strand, for example, by hybridizing to a target. The term synthetic nucleoside, for the purpose of the present invention, refers to a modified nucleoside. Representative modifications include modification of a heterocyclic base portion of a nucleoside to give a non-naturally occurring nucleobase, a sugar portion of a nucleoside, or both simultaneously.

In compounds of Formula II, III, etc., which contain B as a substituent, it is intended to indicate a nucleobase. Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T.

Crooke and B. Lebleu, CRC Press, 1993, in Englisch et al., *Angewandte Chemie,* International Edition, 1991, 30, 613–722 (see especially pages 622 and 623, and in the *Concise Encyclopedia of Polymer Science and Engineering,* J. I. Kroschwitz Ed., John Wiley & Sons, 1990, pages 858–859, Cook, P. D., *Anti-Cancer Drug Design,* 1991, 6, 585–607, each of which are hereby incorporated by reference in their entirety. The term "nucleosidic base" is further intended to include heterocyclic compounds that can serve as like nucleosidic bases including certain 'universal bases' that are not nucleosidic bases in the most classical sense but serve as nucleosidic bases. Especially mentioned as a universal base is 3-nitropyrrole.

Representative 2' sugar modifications (position $R^7$) amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Sugars having O-substitutions on the ribosyl ring are also amenable to the present invention. Representative substitutions for ring O include S, $CH_2$, CHF, and $CF_2$, see, e.g., Secrist, et al., *Abstract 21, Program & Abstracts, Tenth International Roundtable, Nucleosides, Nucleotides and their Biological Applications,* Park City, Utah, Sep. 16–20, 1992, hereby incorporated by reference in its entirety.

As used herein the term "2'-substituent group" includes groups attached to the 2' position of the ribosyl moiety with or without an oxygen atom. 2'-Sugar modifications amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., *Anti-Cancer Drug Design,* 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Additional 2' sugar modifications amenable to the present invention include 2'-SR and 2'-$NR_2$ groups, where each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.,* 1997, 62, 3415–3420. 2'-$NR_2$ nucleosides are disclosed by Goettingen, M., *J. Org. Chem.,* 1996, 61, 6273–6281; and Polushin et al., *Tetrahedron Lett.,* 1996, 37, 3227–3230.

Further representative 2'-O— sugar modifications amenable to the present invention include those having one of formula XII or XIII:

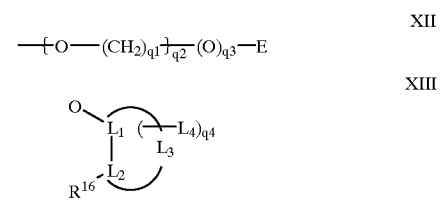

$R^7$, at each occurrence, is indepedently H, hydroxyl, $C_1$–$C_{20}$ alkyl, $C_3$–$C_{20}$ alkenyl, $C_2$–$C_{20}$ alkynly, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, diulfide, silyl, aryl, heterocycle, carbocycle, intercalator, reporter molecule, conjugate, polyamine, polyamide, polyalkylene glycol, polyether, or one of formula XII or XIII:

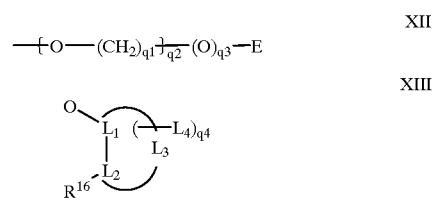

wherein

E is selected from $C_1$–$C_{10}$ alkyl, N $(R^{15})(R^{17})$ and N=C $(R^{15})(R^{17})$;

$R^{15}$ and $R^{17}$ is independently selected from H, $C_1$–$C_{10}$ alkyl, dialkylaminoalkyl, a nitrogen protecting group, a tethered or untethered conjugate group, a linker to a solid support, or alternatively $R^{15}$ and $R^{17}$, together, are joined in a nitrogen protecting group or a ring structure that can include at least one additional heteroatom selected from N and O;

$q^1$ is from 1 to 10;

$q^2$ is from 1 to 10;

$q^3$ is 0 or 1;

$R^{16}$ is $OR^{18}$, $SR^{18}$, or $N(R^{18})_2$;

$R^{18}$ is selected independently from H, $C_1$–$C_8$ alkyl, $C_1$–$C_8$ haloalkyl, C(=NH)N(H)$R^{19}$, C(=O)N(H)$R^{19}$ and OC(=O)N(H)$R^{19}$;

$R^{19}$ is H or $C_1$–$C_8$ alkyl;

$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

L$_4$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$^{15}$)(R$^{17}$) OR$^{15}$, halo, SR$^{15}$ or CN; and q$^4$ is, 0, 1 or 2;

Representative 2'-O— sugar substituents of formula XII are disclosed in U.S. patent application Ser. No.: 09/130, 973, filed Aug. 7, 1998, entitled Capped 2'-Oxyethoxy Oligonucleotides, hereby incorporated by reference in its entirety.

Representative cyclic 2'-O— sugar substituents of formula XIII are disclosed in U.S. patent application Ser. No.: 09/123,108, filed Jul. 27, 1998, entitled RNA Targeted 2'-Modified Oligonucleotides that are Conformationally Preorganized, hereby incorporated by reference in its entirety.

Sugars having O-substitutions on the ribosyl ring are also amenable to the present invention. Representative substitutions for ring O include S, CH$_2$, CHF, and CF$_2$, see, e.g., Secrist, et al., *Abstract 21, Program & Abstracts, Tenth International Roundtable, Nucleosides, Nucleotides and their Biological Applications,* Park City, Utah, Sep. 16–20, 1992, hereby incorporated by reference in its entirety. Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyloxycholesterol moiety (Crooke et al., *J. Pharmacol. Exp. Ther.,* 1996, 277, 923).

When any variable (for example, but not limited to R$^1$, etc.) occurs more than one time in any constituent or in any formula, its definition on each occurrence is independent of its definition at every other occurrence. Thus, for example, if more than one R$^1$ is substituted on phenyl, R$^1$ at each occurrence is selected independently from the defined list of possibilities for R$^1$. It will be well understood by the skilled artisan that the protecting groups of the present invention, as well as the monomer units described herein may be repeated in certain oligomeric compounds. The selection of variables of such units are chosen independently at each occurrence, when, for example, more than one protecting group or monomer unit occurs in a oligomeric chain.

Combinations of substituents and/or variables are permissible only if such combinations result in stable compounds. By stable compounds or stable structure it is meant herein a compound that is sufficiently robust to survive isolation to any useful degree.

As used herein, the term "substituted" means that one or more hydrogen on the designated atom is replaced with a selection from the indicated group, provided that the designated atom's valency is not exceeded, and that the substitution results in a stable compound. When a substituent or substituents appears in a structure to be attached to a phenyl ring, those substituents may take any position which is chemically feasible, as a point of attachment on the phenyl ring.

Any carbon range used herein, such as "C$_{v-w}$" is intended to mean a minimum of "v" carbons and a maximum of "y" carbons, inclusive of all carbon values and ranges between.

As used herein, the term "alkyl" is intended to include both straight-chain and branched-chain saturated aliphatic hydrocarbon groups containing the specified number of carbon atoms. For example, and without limitation, C$_{1-4}$ alkyl includes methyl, ethyl, n-propyl, i-propyl, n-butyl, i-butyl, s-butyl, and t-butyl; C$_{1-10}$ includes, but is not limited to C$_{1-4}$ alkyl, pentyl, hexyl, heptyl, octyl, nonyl, decyl, and isomers thereof. Alkyl and alkylene groups of the present invention may also be further substituted. Representative alkyl substituents are disclosed in U.S. Pat. No. 5,212,295, at column 12, lines 41–50, hereby incorporated by reference in its entirety.

As used herein, "alkylene" is intended to mean a bridging alkyl group, i.e. —CH$_2$—, which includes both straight-chain and branched-chain saturated aliphatic hydrocarbon bridging groups containing the specified number of carbon atoms.

As used herein, "alkenyl" refers to hydrocarbon chains of either straight or branched configuration, and one or more unsaturated carbon—carbon bonds which may occur at any stable point along the chain. For example, and without limitation C$_{2-4}$ alkenyl includes ethenyl, 1-propenyl, 2-propenyl, 1-butenyl, 2-butenyl, 3-butenyl, 1,3-butadienyl, and the like.

As used herein, "alkynyl" refers to hydrocarbon chains of either straight or branched configuration, and one or more triple carbon—carbon bonds which may occur at any stable point along the chain. For example, and without limitation C$_{2-4}$ alkynyl includes ethynyl, propynyl, and butynyl.

As used herein, "cycloalkyl" or "carbocycle" is intended to include saturated ring groups, including mono-, bi-, or polycyclic ring systems. For example, and without limitation, C$_{3-6}$ cycloalkyl includes cyclopropyl, cyclobutyl, cyclopentyl, and cyclohexyl.

As used herein, "aryl" refers to aromatic cyclic compounds including, but not limited to, phenyl, naphthyl, anthracyl, phenanthryl, pyrenyl, and xylyl.

As used herein, "heterocycle", "heterolcyclic" or "heterocyclic system" is intended to mean a stable 5 to 10 membered monocyclic or 5 to 10 membered bicyclic ring which may be saturated, partially saturated or unsaturated, and which consists of carbon atoms and from 1 to 3 heteroatoms independently selected from the group consisting of N, O and S, wherein the nitrogen and sulfur may be optionally oxidized, and the nitrogen may be optionally quaternized, and further including any bicyclic group in which any of the above defined heterocyclic rings is fused to a benzene ring. The heterocyclic rings of the present invention may be attached to their pendant group at any heteroatom or carbon atom which results in a stable structure.

Examples of such heterocycles include, but are not limited to 2-pyrrolidonyl, 2H-pyrrolyl, 4-piperidonyl, 6H-1,2,5-thiadiazinyl, 2H,6H-1,5,2-dithiazinyl, 1,2,3-thiadiazolyl, 1,2,4-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, furanyl, furazanyl, imidazolidinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, piperazinyl, piperidinyl, pteridinyl piperidonyl, purinyl, pyranyl, pyrazinyl, pyrazolidinyl, pyrazolyl, pyridazinyl, pyridinyl, pyridyl, pyrimidinyl, pyrrolidinyl, pyrrolinyl, pyrrolyl, and tetrahydrofuranyl. Also included are fused ring and spirocompounds containing, for example, the above heterocycles.

SYNTHESIS

In certain embodiments of the invention $R^6$ and $R^{10}$ may be a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y, 1991, Chapter 1, pages 1–23, hereby incorporated by reference in its entirety.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, hereby incorporated by reference in its entirety), TentaGel Support—an aminopolyethyleneglycol derivatized support (see, e.g., Wright, et al., *Tetrahedron Letters* 1993, 34, 3373, hereby incorporated by reference in its entirety) and Poros—a copolymer of polystyrene/divinylbenzene.

In some preferred embodiments of the invention $R^6$ and $R^{10}$ can be a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, *Protective Groups in Organic Synthesis*, Chapter 2, 2d ed, John Wiley & Sons, New York, 1991, each of which are hereby incorporated by reference in their entirety. Preferred protecting groups used for $R^{10}$, $R^6$ and $R^{6a}$ include dimethoxytrityl (DMT), monomethoxytrityl, 9-phenylxanthen-9-yl (Pixyl) and 9-(p-methoxyphenyl)xanthen-9-yl (Mox). The $R^{10}$ or $R^6$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or other groups, such as, for example, 2'-alkoxy groups (e.g., when $R^{7b}$ is $NR^{9a}R^{9b}$). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Sulfurizing agents used during oxidation to form phosphorothioate and phosphorodithioate linkages include Beaucage reagent (see e.g. Iyer, R. P., et.al., *J. Chem. Soc.*, 1990, 112, 1253–1254, and Iyer, R. P., et.al., *J. Org. Chem.*, 1990, 55, 4693–4699); tetraethylthiuram disulfide (see e.g., Vu, H., Hirschbein, B. L., *Tetrahedron Lett.*, 1991, 32, 3005–3008); dibenzoyl tetrasulfide (see e.g., Rao, M. V., et.al., *Tetrahedron Lett.*, 1992, 33, 4839–4842); di(phenylacetyl)disulfide (see e.g., Kamer, P. C. J., *Tetrahedron Lett.*, 1989, 30, 6757–6760); Bis(O,O-diisopropoxy phosphinothioyl)disulfids (see Stec et al., *Tetrahedron Lett.*, 1993, 34, 5317–5320); 3-ethoxy-1,2,4-dithiazoline-5-one (see *Nucleic Acids Research*, 1996 24, 1602–1607, and *Nucleic Acids Research*, 1996 24, 3643–3644); Bis(p-chlorobenzenesulfonyl)disulfide (see *Nucleic Acids Research*, 1995 23, 4029–4033); sulfur, sulfur in combination with ligands like triaryl, trialkyl, triaralkyl, or trialkaryl phosphines. The foregoing references are hereby incorporated by reference in their entirety.

Useful oxidizing agents used to form the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

Oligonucleotides or oligonucleotide analogs according to the present invention hybridizable to a specific target preferably comprise from about 5 to about 50 monomer subunits. It is more preferred that such compounds comprise from about 10 to about 30 monomer subunits, with 15 to 25 monomer subunits being particularly preferred. When used as "building blocks" in assembling larger oligomeric compounds (i.e., as synthons of Formula II), smaller oligomeric compounds are preferred. Libraries of dimeric, trimeric, or higher order compounds of general Formula II can be prepared for use as synthons in the methods of the invention. The use of small sequences synthesized via solution phase chemistries in automated synthesis of larger oligonucleotides enhances the coupling efficiency and the purity of the final oligonucloetides. See for example: Miura, K., et al., *Chem. Pharm. Bull.*, 1987, 35, 833–836; Kumar, G., and Poonian, M. S., *J. Org. Chem.*, 1984, 49, 4905–4912; Bannwarth, W., *Helvetica Chimica Acta*, 1985, 68, 1907–1913; Wolter, A., et al., *nucleosides and nucleotides*, 1986, 5, 65–77, each of which are hereby incorporated by reference in their entirety.

Protecting groups of Formula I include, but are not limited to, compounds containing acylaminoalkyl, thioacyl aminoalkyl (including thioureaalkyl), and carbamoylalkyl functionalities. Such functionalities may be prepared by methods well known to one skilled in the art, as well as methods taught herein. By way of general guidance, if protecting groups containing an acylaminoalkyl functionality are desired, the precursors may be obtained by reaction of an appropriately substituted amine with an appropriately substituted benzoylhalide (Scheme 1).

Scheme 1

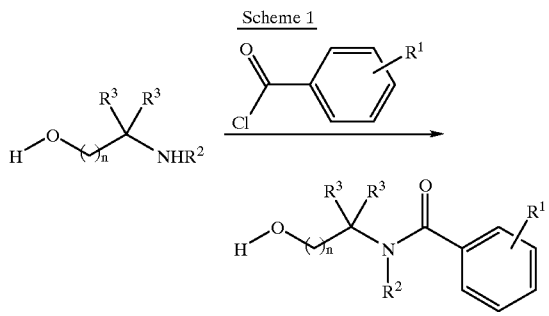

If protecting groups containing a thioacylaminoalkyl functionality are desired, the precursors may be obtained by reaction of an appropriately substituted amine with an appropriately substituted thiobenzoylthioglycolic acid derivative (or thioisocyanate)(Scheme 2).

Scheme 2

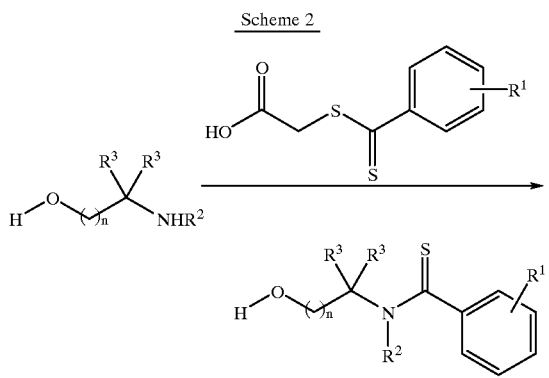

If protecting groups containing the carbamoyl-aminoalkyl or thioureaalkyl functionality are desired, the precursors may be obtained by reaction of an appropriately substituted alcohol with an appropriately substituted isocyanate or thioisocyanate, respectively (Scheme 3).

Scheme 3

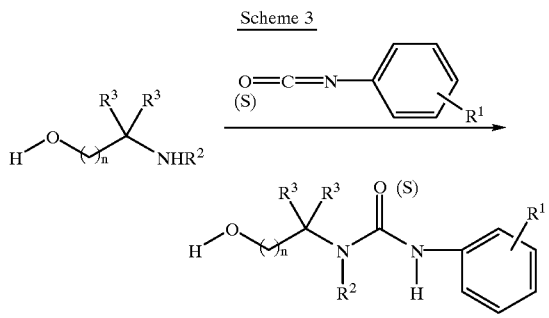

As will be readily understood to the skilled artisan, in each of Schemes 1–3 the alcoholic starting material (HOR) may be substituted with the analogous sulfur derivate (HSR) in order to afford alkyl chains terminating in —SH.

Each protecting group precursor may be employed by methods known in the art of oligonucleotide synthesis. In one aspect of the invention, the compounds of the invention are used to modulate RNA or DNA, which code for a protein whose formation or activity it is desired to modulate. The targeting portion of the composition to be employed is, thus, selected to be complementary to the preselected portion of DNA or RNA, that is to be hybridizable to that portion.

Compounds of Formula II may be prepared by reaction of a protected nucleoside having Formula V:

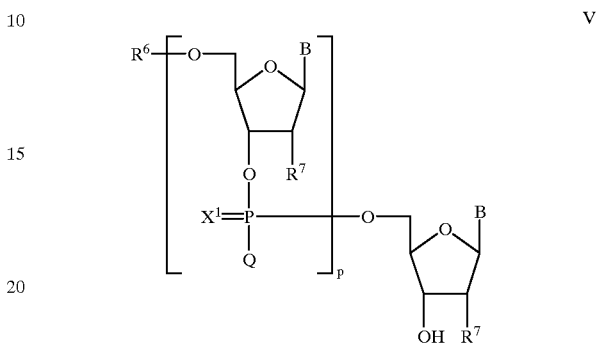

with a chlorophosphine compound of formula $ClP(R^8)_2$ in the presence of a base, followed by reaction with the protecting group precursors of Formula I-i:

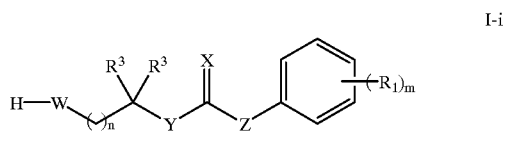

in the presence of an acid to form the compound of Formula II:

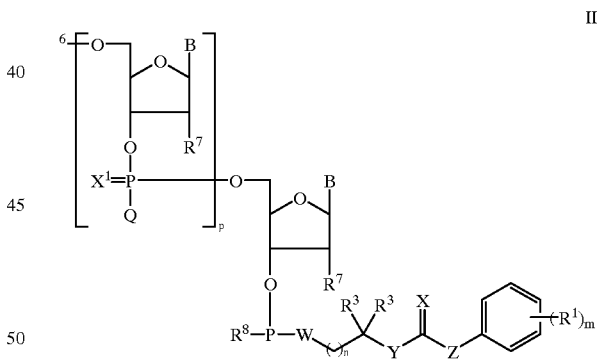

Suitable bases include those known in the art to serve as acid scavengers. Examples of such bases include, but are not limited to, amine bases of formula $(C_{1-10}\ alkyl)_3N$ and aromatic amines. Most preferred is N,N-diisopropylethylamine. Suitable acids include those known in the art to be useful for coupling of phosphoramidites, including, for example, diisopropylammonium tetrazolide. In preferred embodiments, W is oxygen, $R^4$ is hydrogen, $R^3$ is hydrogen, Y is $CH_2$, X is oxygen, Z is $NR^2$, $R^2$ is H or $C_{1-3}$ alkyl, m is 0 or 1, and $R^1$ is selected from $OCH_3$, $NO_2$, and $N(CH_3)_2$.

It will be appreciated by one skilled in the art that variations on this general approach are possible, and are contemplated by the present invention. For example, the compound of Formula II may be an oligomeric compound which includes a single mononucleotide. Moreover, such compounds may also be formed by reaction of the compound of Formula V with a compound of Formula VI:

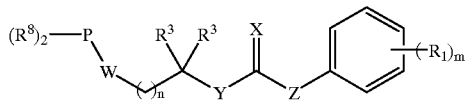
VI in the presence of an acid, wherein the compound of Formula VI is formed by the reaction of a compound of Formula I-i with a chlorophosphine compound of formula $ClP(R^8)_2$ in the presence of a base.

The protected compounds of the present invention may react further in accordance with methods taught herein, and those understood to the artisan versed in oligonucleotide synthesis. By way of general guidance, a compound of Formula II:

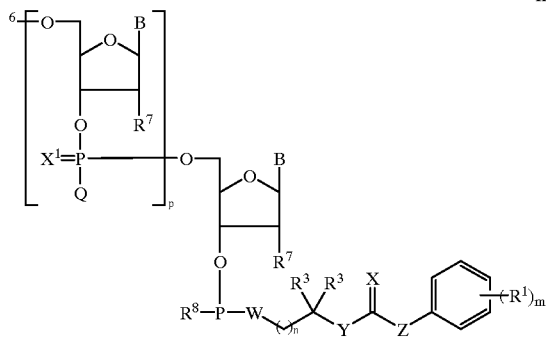
II wherein $R^6$, $R^7$, $R^8$, $X^1$, B, p, and Q are defined herein, may be reacted with a compound of Formula III:

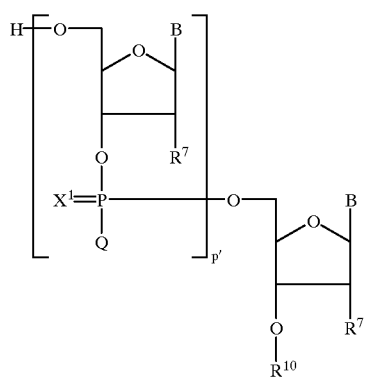
III wherein $R^{10}$, $R^6$, $R^{10}$, and p' are defined herein, to form an oligomeric compound of having a moiety of Formula X:

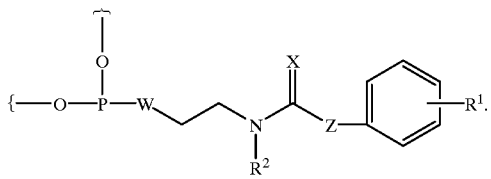
X

Also provided in certain preferred embodiments, are compounds of Formula IX:

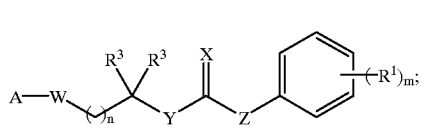
IX wherein A, W, X, Y, Z, $R^1$, $R^3$ and $R^4$ are described herein.

Most preferred compounds of formula IX and X are those in which $R^3$ is H, Y is N—$CH(CH_3)_2$, X is O, Z is a bond and $R^1$ is $OCH_3$ in the para position.

In the compounds and methods of the present inventon, $X_1$ and $X_2$ can each independently be O or S. Thus, compounds having chiral phosphorus linkages are contemplated by the present invention. See Stec, W. J., and Lesnikowski, Z. J., in *Methods in Molecular Biology* Vol. 20: *Protocols for Oligonucleotides and Analogs,* S. Agrawal, Ed., Humana Press, Totowa, N.J. (1993), at Chapter 14. See also Stec, W. J. et al., *Nucleic Acids Research,* Vol. 19, No. 21, 5883–5888 (1991); and European Patent Application EP 0 506 242 A1, each of which are hereby incorporated by reference in their entirety.

The oligomeric compounds of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

As will be recognized, the steps of certain processes of the present invention need not be performed any particular number of times or in any particular sequence. Additional objects, advantages, and novel features of this invention will become apparent to those skilled in the art upon examination of the following synthetic teachings, prophetic examples, and working examples which are intended to be illustrative of the present invention, and not limiting thereof.

Methods for coupling compounds of Formula II and Formula III of the present invention include both solution phase and solid phase chemistries. Representative solution phase techniques are described in U.S. Pat. No. 5,210,264, which is assigned to the assignee of the present invention. In preferred embodiments, the methods of the present invention are employed for use in iterative solid phase oligonucleotide synthetic regimes. Representative solid phase techniques are those typically employed for DNA and RNA synthesis utilizing standard phosphoramidite chemistry, (see, e.g., Protocols For Oligonucleotides And Analogs, Agrawal, S., ed., Humana Press, Totowa, N.J., 1993, hereby incorporated by reference in its entirety). A preferred synthetic solid phase synthesis utilizes phosphoramidites as activated phosphate compounds. In this technique, a phosphoramidite monomer is reacted with a free hydroxyl on the growing oligomer chain to produce an intermediate phosphite compound, which is subsequently oxidized to the $P^v$ state using standard methods. This technique is commonly used for the synthesis of several types of linkages including phosphodiester, phosphorothioate, and phosphorodithioate linkages.

Typically, the first step in such a process is attachment of a first monomer or higher order subunit containing a protected 5'-hydroxyl to a solid support, usually through a linker, using standard methods and procedures known in the art. The support-bound monomer or higher order first synthon is then treated to remove the 5'-protecting group, to form a compound of Formula III wherein $R^{10}$ is a linker connected to a solid support. Typically, this is accomplished by treatment with acid. The solid support bound monomer is then reacted with a compound of Formula II to form a compound of Formula IV, which has a phosphite or thiophosphite linkage of Formula I. In preferred embodiments, synthons of Formula II and Formula III are reacted under anhydrous conditions in the presence of an activating agent such as, for example, 1H-tetrazole, 5-(4-nitrophenyl)-1H-tetrazole, or diisopropylamino tetrazolide.

In preferred embodiments, phosphite or thiophosphite compounds containing a linkage of Formula I are oxidized or sulfurized as shown below to produce compounds having a linkage of Formula XII, where W and $X^1$ can each be O or S:

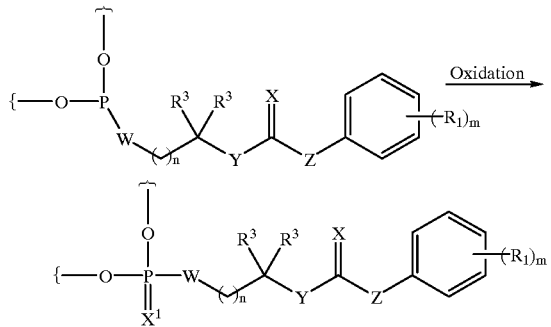

Choice of oxidizing or sulfurizing agent will determine whether the linkage of Formula I will be oxidized or sulfurized to a phosphotriester, thiophosphotriester, or a dithiophosphotriester linkage.

Treatment with an acid removes the 5'-hydroxyl protecting group, and thus transforms the solid support bound oligomer into a further compound of Formula III wherein $R^{6a}$ is hydrogen, which can then participate in the next synthetic iteration; i.e., which can then be reacted with a further compound of Formula II. This process is repeated until an oligomer of desired length is produced.

The completed oligomer is then cleaved from the solid support. The cleavage step, which can precede or follow deprotection of protected functional groups, will yield a compound having Formula IV wherein $R^{10}$ is hydrogen. During cleavage, the linkages between monomeric subunits are converted from phosphotriester, thiophosphotriester, or dithiophosphotriester linkages to phosphodiester, phosphorothioate, or phosphorodithioate linkages. This conversion is effected through the loss of an oxygen or sulfur protecting group of the present invention.

A wide variety of bases can be used to initiate the removal of the protecting groups of the present invention. These include aqueous ammonium hydroxide, aqueous methylamine, DBU (1,8-diazabicyclo[5.4.0]undec-7-ene) and carbonates containing counterions such as lithium, potassium, sodium, and cesium. Most preferred is potassium carbonate and ammonia. Removal of the protecting groups may be performed in a variety of suitable solvents. These solvents include those known to be suitable for protecting group removal in oligonucleotide synthesis. In the case of ammonia, water is the preferred solvent, whereas when using carbonates, alcohols are preferred. Methanol is most preferred. In certain preferred embodiments, conditions for removal of the oxygen or sulfur protecting group also effect cleavage of the oligomeric compound from the solid support.

EXAMPLES

By using protocols and procedures taught herein, in conjunction with those well known in the art, protected nucleosides 1–8 (Table 1) were prepared and converted to nucleoside phosphoramidites 15–6 (Table 2). Analogously, protected nucleosides 9–11 (Table 3) were prepared and converted to phosphoramidites 27–29 (Table 4), and protected nucleosides 12–14 (Table 5) were prepared and converted to phophoramidites 30–32 (Table 6). These phosphoramidites were subsequently employed in oligonucleotide synthesis. The solid bound support was then deprotected with either ammonia or potassium carbonate in methanol (Table 7) to afford deoxyribonucleotides and their phosphorothiate analogs. The following examples are presented for illustrative purposes only, and should not be taken as limiting of the inventors' scope.

Example 1

N-Isopropyl-N-(2-hydroxyethyl)-4-methoxybenzamide, 8

Anisoyl chloride (17.1 g, 0.1 mol) in THF (100 mL) was added dropwise to a solution of N-isopropylaminoethanol (41.3 g, 0.4 mol) in THF (200 mL) under magnetic stirring at 4 to 10° C. The reaction mixture was stirred for 2 h at room temperature, and the solvent was evaporated in vacuo. The residue was dissolved in ice-cold water (200 mL), and the solution was neutralized with conc. hydrochloric acid. The emulsion was extracted with ethyl acetate (3' 150 mL). Extracts were washed with saturated aqueous NaCl (3' 50 mL), dried over $Na_2SO_4$, and evaporated to a solid. Recrystallization from warm toluene-hexanes gave pure 8 as white crystals (20.5 g, 88%). $^1$H NMR (CDCl$_3$): 7.32 (2H, d, J=8.6 Hz); 6.89 (2H, d, J=8.6 Hz); 4.40 (1H, br. s); 4.09 (1H, m); 3.80 (3H, s); 3.90–3.70 (1H, m); 3.53 (2H, t, J=4.6 Hz); 1.13

(6H, d, J=6.8 Hz). $^{13}$C NMR (CDCl$_3$): 173.56 (C=O); 160.60 (C—OMe); 128.71 [C—C(O)]; 128.16 (Arom. CH); 113.89 (Arom. CH); 63.69 (CH$_2$OH); 55.39 (OCH$_3$); 50.60 (N—CH); 44.45 (N—CH$_2$); 21.19 (C—CH$_3$).

Example 2

N-(Isopropyl)-N-[(4-methoxy)benzoyl]aminoethyl [5'-O-(4,4'-dimethoxytrityl)thymidin-3'-yl]N,N-diisopropylphosphoramidite, 22

A solution of chloro bis[(N,N,-diisopropyl)amino] phosphite (3068 mg, 11.5 mmol) in dry CH$_2$Cl$_2$ (25 mL) was added dropwise to a mixture of 5'-O-(4,4'-dimethoxytrityl) thymidine (5446 mg, 10.0 mmol) and N-ethyl-N,N-diisopropylamine (1550 mg, 12.0 mmol) in dry CH$_2$Cl$_2$ (25 mL) under magnetic stirring at −20° C. The reaction mixture was allowed to warm up to room temperature, and the stirring was continued for 1 h. Dry N-(isopropyl)-N-[(4-methoxy)benzoyl]aminoethanol, 8, (2780 mg, 12 mmol) was added followed by 1H-tetrazole (0.45 M in MeCN; 13.3 mL, 6.0 mmol). The resulting mixture was kept at room temperature for 2 h and found to reach completeness by $^{31}$P NMR. Aqueous NaHCO$_3$ (5%; 20 mL) was added, the emulsion was diluted with saturated aqueous NaCl (50 mL), and the product was extracted with ethyl acetate (3' 100 mL). Extracts were washed with saturated aqueous NaCl (3' 50 mL), dried over Na$_2$SO$_4$, and evaporated to dryness. The residue was dissolved in toluene (50 mL), applied on a silica gel column, and separated eluting with a gradient from 30:65:5 to 90:5:5 ethyl acetate/hexane/triethylamine. Collected fractions were evaporated, co-evaporated with dry MeCN (2' 50 mL), and dried on an oil pump to give fast diastereomer 22f (477 mg), slow diastereomer 22s (579 mg), and their mixture (6966 mg) totaled in 8022 mg (88%) of 22. $^{31}$P and $^{13}$C NMR data are presented in Table 1 and Table 2, correspondingly.

Fast diastereomer, 22f, $^1$H NMR (CDCl$_3$): 7.61 (1H, s); 7.40–7.16 (12H, m); 6.90–6.74 (6H, m); 6.39 (1H, dd, J=8.0, 5.7 Hz); 4.63 (1H, m); 4.19 (1H, m); 3.77 (3H, s); 3.74 (6H, s); 3.95–3.26 (9H, m); 2.45 (1H, ddd, J=13.0, 5.4, 1.5 Hz); 2.28 (1H, ddd, 13.0, 7.2, 6.18 Hz); 1.35 (3H, s); 1.20–1.10 (18H, m) Slow diastereomer, 22s, $^1$H NMR (CDCl$_3$): 7.60 (1H, s); 7.41–7.18 (12H, m); 6.90–6.74 (6H, m); 6.43 (1H, br. t); 4.66 (1H, m); 4.14 (1H, m); 3.79 (3H, s); 3.76 (6H, s); 3.96–3.25 (9H, m); 2.64–2.48 (1H, m); 2.42–2.20 (1H, m); 1.40 (3H, s); 1.28–1.0 (18H, m).

Example 3

N-Benzoylaminoethyl[5'-O-(4,4'-dimethoxytrityl) thymidin-3'-yl]N,N-diisopropylphosphoramidite, 15

Compound 15 was synthesized analogously from 5'-O-(4,4'-dimethoxytrityl)thymidine (1089 mg, 2.0 mmol), chloro bis[(N,N,-diisopropyl)amino]phosphite (640 mg, 2.4 mmol), and N-benzoylaminoethanol, 1 (413 mg, 2.5 mmol). Column separation gave fast diastereomer, 15f (317 mg), slow diastereomer, 15s (435 mg) and their mixture (516 mg) to total in 1268 mg (75.6%) of 15. $^{31}$P and $^{13}$C NMR data are presented in Table 1 and Table 2, correspondingly.

Fast diastereomer, 15f, $^1$H NMR (CDCl$_3$): 9.05 (1H, br. s); 7.69 (2H, m); 7.65 (1H, d, J=0.9 Hz); 7.50–7.20 (12H, m); 6.9–6.8 (4H, m); 6.50 (1H, br. t); 6.40 (1H, dd, J=7.5, 5.8 Hz); 4.67 (1H, m); 4.16 (1H, m); 3.77 (6H, s); 3.70–3.42 (7H, m); 3.31 (1H, dd, J=10.4, 2.4 Hz); 2.47 (1H, ddd, J=13.2, 5.8, 2.5 Hz); 2.31 (1H, ddd, J=13.2, 7.5, 7.5 Hz); 1.42 (3H, s); 1.15 (12H, d, J=6.5 Hz)

Slow diastereomer, 15s, $^1$H NMR (CDCl$_3$): 9.06 (1H, br. s.); 7.79 (1H, br.s); 7.77 (1H, br. s); 7.60 (1H, br. s); 7.50–7.20 (13H, m); 6.9–6.8 (4H, m); 6.50 (1H, br. t); 6.42 (1H, dd, J=8.2, 5.9 Hz); 4.65 (1H, m); 4.15 (1H, m); 3.78 (6H, s); 3.70–3.41 (7H, m); 3.38–3.20 (1H, m); 2.66–2.50 (1H, m); 2.40–2.18 (1H, m); 1.44 (3H, s); 1.13 (6H, d, J=6.8 Hz); 1.04 (6H, d, J=6.8 Hz).

Example 4

N-[(3-Nitro)benzoyl]aminoethyl[5'-O-(4,4'-dimethoxytrityl)thymidin-3'-yl]N,N-diisopropylphosphoramidite, 16

Compound 16 was synthesized analogously from 5'-O-(4,4'-dimethoxytrityl)thymidine (1089 mg, 2.0 mmol), chloro bis[(N,N,-diisopropyl)amino]phosphite (587 mg, 2.2 mmol), and N-[(3-nitro)benzoyl]aminoethanol, 2 (483 mg, 2.3 mmol). Column separation gave fast diastereomer, 16f (404 mg), slow diastereomer, 16s (379 mg) and their mixture (294 mg) to total in 1077 mg (61.0%) of 16. $^{31}$P and $^{13}$C NMR data are presented in Table 1 and Table 2, correspondingly.

Fast diastereomer, 16f, $^1$H NMR (CDCl$_3$): 9.17 (1H, br. s); 8.56 (1H, t, J=1.9 Hz); 8.33–8.27 (1H, m); 8.08–7.99 (1H, m); 7.65–7.50 (2H, m); 7.42–7.20 (10H, m); 6.90–6.75 (4H, m); 6.36 (1H, dd, J=7.3, 6.0 Hz); 4.67 (1H, m); 4.18 (1H, m); 3.77 (6H, s); 3.85–3.26 (8H, m); 2.46 (1H, ddd, 13.6, 6.0, 2.8 Hz); 2.33 (1H, ddd, J=13.6, 7.3, 7.3 Hz); 1.41 (3H, s); 1.16 (6H, d, J=6.6 Hz); 1.15 (6H, d, J=6.4 Hz)

Slow diastereomer, 16s, $^1$H NMR (CDCl$_3$): 9.25 (1H, br. s); 8.65 (1H, t, J=1.8 Hz); 8.33–8.18 (2H, m); 7.68–7.55 (2H, m); 7.45–7.20 (10H, m); 6.90–6.75 (4H, m); 6.37 (1H, dd, J=8.6, 5.1 Hz); 4.63 (1H, m); 4.16 (1H, m); 3.78 (6H, s); 3.90–3.20 (8H, m); 2.64 (1H, dd, 13.6, 5.1 Hz); 2.27 (1H, ddd, J=13.6, 8.6, 5.7 Hz); 1.45 (3H, s); 1.14 (6H, d, J=6.6 Hz); 1.06 (6H, d, J=5.5 Hz).

Example 5

N-[(4-methoxy)benzoyl]aminoethyl[5'-O-(4,4'-dimethoxytrityl)thymidin-3'-yl]N,N-diisopropylphosphoramidite, 17

Compound 17 was synthesized analogously from 5'-O-(4,4'-dimethoxytrityl)thymidine (1089 mg, 2.0 mmol), chloro bis[(N,N,-diisopropyl)amino]phosphite (587 mg, 2.2 mmol), and N-[(4-methoxy)benzoyl]aminoethanol, 3 (449 mg, 2.3 mmol). Column separation gave fast diastereomer, 17f (295 mg), slow diastereomer, 17s (420 mg) and their mixture (481 mg) to total in 1196 mg (68.8%) of 17. $^{31}$P and $^{13}$C NMR data are presented in Table 1 and Table 2, correspondingly.

Fast diastereomer, 17f, $^1$H NMR (CDCl$_3$): 9.35 (1H, br. s); 7.70–7.60 (3H, m); 7.44–7.16 (10H, m); 6.90–6.76 (6H, m); 6.46–6.35 (2H, m); 4.67 (1H, m); 4.16 (1H, m); 3.81 (3H, s); 3.80 (6H, s); 3.70–3.42 (7H, m); 3.31 (1H, dd, J=10.6, 2.7 Hz); 2.50 (1H, ddd, J=13.7, 5.8, 2.9); 2.33 (1H, ddd, J=13.7, 6.8, 6.8); 1.42 (3H, s); 1.14(12H, d, J=6.7 Hz).

Slow diastereomer, 17s, $^1$H NMR (CDCl$_3$): 9.20 (1H, br. s); 7.74 (2H, d, J=8.7 Hz); 7.59 (1H, s); 7.43–7.20 (10H, m); 6.91–6.78 (6H, m); 6.71 (1H, br. t); 6.41 (1H, dd, J=7.6, 5.5 Hz); 4.63 (1H, m); 4.14 (1H, m); 3.80 (3H, s); 3.78 (6H, s); 3.92–3.20 (8H, m); 2.56 (1H, dd, J=13.2, 5.5 Hz); 2.24 (1H, ddd, J=13.2, 7.6, 6.2 Hz); 1.42 (3H, s); 1.12 (6H, d, J=6.3 Hz); 1.04 (6H, d, J=6.8 Hz).

Example 6

N-Benzoyl-2-methyl-2-aminopropyl[5'-O-(4,4'-dimethoxytrityl)thymidin-3'-yl]N,N-diisopropylphosphoramidite, 18

Compound 18 was synthesized analogously from 5'-O-(4,4'-dimethoxytrityl)thymidine (1089 mg, 2.0 mmol), chloro bis[(N,N,-diisopropyl)amino]phosphite (640 mg, 2.4 mmol), and N-benzoyl-2-methyl-2-aminopropanol, 4 (483 mg, 2.5 mmol). Column separation gave fast diastereomer, 18f (399 mg), slow diastereomer, 18s (407 mg) and their mixture (590 mg) to total in 1396 mg (80.5%) of 18. $^{31}$P and $^{13}$C NMR data are presented in Table 1 and Table 2, correspondingly.

Fast diastereomer, 18f, $^1$H NMR (CDCl$_3$): 8.79 (1H, br. s); 7.77–7.61 (2H, m); 7.53 (1H, s); 7.45–7.22 (12H, m); 6.88–6.76 (4H, m); 6.39 (1H, br. t); 6.36 (1H, dd, J=7.5, 6.5 Hz); 4.71 (1H, m); 4.13 (1H, m); 3.79 (6H, s); 3.90–3.38 (5H, m); 3.36–3.22 (1H, m); 2.6–2.1 (2H, m); 1.47 (3H, s); 1.43 (3H, s); 1.39 (3H, s); 1.14(6H, d, J=6.5 Hz); 1.04 (6H, d, J=6.6 Hz).

Slow diastereomer, 18s, $^1$H NMR (CDCl$_3$): 8.79 (1H, br. s); 7.77–7.61 (2H, m); 7.53 (1H, s); 7.45–7.22 (12H, m); 6.88–6.76 (4H, m); 6.39 (1H, br. t); 6.36 (1H, dd, J=7.2, 5.5 Hz); 4.63 (1H, m); 4.11 (1H, m); 3.78 (6H, s); 3.92–3.40 (5H, m); 3.36–3.22 (1H, m); 2.6–2.1 (2H, m); 1.49 (3H, s); 1.40 (6H, s); 1.17 (6H, d, J=6.7 Hz); 1.14 (6H, d, J=6.6 Hz).

Example 7

N-Methyl-N-benzoylaminoethyl[5'-O-(4,4'-dimethoxytrityl)thymidin-3'-yl]N,N-diisopropylphosphoramidite, 19

Compound 19 was synthesized analogously from 5'-O-(4,4'-dimethoxytrityl)thymidine (1089 mg, 2.0 mmol), chloro bis[(N,N,-diisopropyl)amino]phosphite (640 mg, 2.3 mmol), and N-methyl-N-benzoylaminoethanol, 5 (412 mg, 2.3 mmol). Column separation gave fast diastereomer, 19f (282 mg), slow diastereomer, 19s (518 mg) and their mixture (546 mg) to total in 1346 mg (78.9%) of 19. $^{31}$P and 13C NMR data are presented in Table 1 and Table 2, correspondingly.

Fast diastereomer, 19f, $^1$H NMR (CDCl$_3$): 8.94 (1H, br. s); 7.64 (1H, m); 7.45–7.20 (14H, m); 6.85–6.75 (4H, m); 6.41 (1H, dd, J=7.3, 7.3 Hz); 4.65 (1H, m); 4.16 (1H, m); 3.81 (6H, s); 3.90–3.20 (8H, m); 3.04 and 2.97 (total 3H, br. s); 2.56–2.39 (1H, m); 2.39–2.21 (1H, m); 1.41 (3H, s); 1.15 (12H, m).

Slow diastereomer, 19s, $^1$H NMR (CDCl$_3$): 8.92 (1H, br. s); 7.59 (1H, m); 7.45–7.20 (14H, m); 6.87–6.77 (4H, m); 6.41 (1H, dd, J=7.4, 7.4 Hz); 4.62 (1H, m); 4.14 (1H, m); 3.78 (6H, s); 3.90–3.20 (8H, m); 3.12 and 3.06 (total 3H, br. s); 2.60–2.38 (1H, m); 2.38–2.18 (1H, m); 1.41 (3H, s); 1.18–1.0 (12H, m).

Example 8

N-Methyl-N-[(4-methoxy)benzoyl]aminoethyl[5'-O-(4,4'-dimethoxytrityl)thymidin-3'-yl]N,N-diisopropylphosphoramidite, 20

Compound 20 was synthesized analogously from 5'-O-(4,4'-dimethoxytrityl)thymidine (1089 mg, 2.0 mmol), chloro bis[(N,N,-diisopropyl)amino]phosphite (640 mg, 2.4 mmol) and N-methyl-N-[(4-methoxy)benzoyl]aminoethanol, 6, (523 mg, 2.5 mmol). Column separation gave fast diastereomer 20f (529 mg), slow diastereomer 20s (398 mg), and their mixture (523 mg) totaled in 1450 mg (82.1%) of 20. $^{31}$P and $^{13}$C NMR data are presented in Table 1 and Table 2, correspondingly.

Fast diastereomer, 20f, $^1$H NMR (CDCl$_3$): 9.01 (1H, br. s.); 7.64 (1H, s); 7.45–7.18 (11H, m); 6.9–6.7 (6H, m); 6.40 (1H, dd, J=7.5, 5.9 Hz); 4.65 (1H, m); 4.16 (1H, m); 3.79 (3H, s); 3.77 (6H, s); 3.90–3.24 (8H, m); 3.01 (3H, s); 2.55–2.38 (1H, m); 2.38–2.20 (1H, m); 1.41 (3H, s); 1.15 (12H, d, J=6.5 Hz).

Slow diastereomer, 20s, $^1$H NMR (CDCl$_3$): 9.13 (1H, br. s.); 7.58 (1H, s); 7.45–7.18 (11H, m); 6.9–6.7 (6H, m); 6.41 (1H, dd, J=7.9, 6.0 Hz); 4.62 (1H, m); 4.12 (1H, m); 3.79 (3H, s); 3.77 (6H, s); 3.90–3.20 (8H, m); 3.01 (3H, s); 2.60–2.41 (1H, m); 2.38–2.18 (1H, m); 1.41 (3H, s); 1.12 (6H, d, J=7.1 Hz); 1.02 (6H, d, J=6.7 Hz).

Example 9

N-Methyl-N-[(4-dimethylamino)benzoyl]aminoethyl [5'-O-(4,4'-dimethoxytrityl)thymidin-3'-yl]N,N-diisopropylphosphoramidite, 21

Compound 21 was synthesized analogously from 5'-O-(4,4'-dimethoxytrityl)thymidine (2178 mg, 4.0 mmol), chloro bis[(N,N,-diisopropyl)amino]phosphite (1280 mg, 4.8 mmol) and N-methyl-N-[(4-dimethylamino)benzoyl]aminoethanol, 7, (1111 mg, 5.0 mmol). Column separation gave fast diastereomer 21f (1068 mg), slow diastereomer 21s (987 mg), and their mixture (1038 mg) totaled in 3093 mg (86.3%) of 21. $^{31}$P and $^{13}$C NMR data are presented in Table 1 and Table 2, correspondingly.

Fast diastereomer, 21f, $^1$H NMR (CDCl$_3$): 8.90 (1H, br. s.); 7.64 (1H, s); 7.45–7.18 (11H, m); 6.90–6.78 (4H, m); 6.68–6.58 (2H, m); 6.40 (1H, br. t); 4.65 (1H, m); 4.16 (1H, m); 3.77 (6H, s); 3.80–3.40 (8H, m); 3.03 (3H, s); 2.95 (6H, s); 2.53–2.38 (1H, m); 2.38–2.20 (1H, m); 1.41 (3H, s); 1.15 (12H, d, J=6.8 Hz).

Slow diastereomer, 20s, $^1$H NMR (CDCl$_3$): 8.75 (1H, br. s.); 7.57 (1H, s); 7.44–7.16 (11H, m); 6.88–6.75 (4H, m); 6.67–6.58 (2H, m); 6.41 (1H, dd, J=7.9, 6.1 Hz); 4.62 (1H, m); 4.11 (1H, m); 3.78 (6H, s); 3.84–3.20 (8H, m); 3.12 (3H, s); 2.96 (6H, s); 2.50 (1H, ddd, J=13.3, 5.4, ≈1 Hz); 2.38–2.18 (1H, m); 1.42 (3H, s); 1.14 (6H, d, J=6.7 Hz); 1.04 (6H, d, J=6.8 Hz).

Example 10

N-(Isopropyl)-N-[(4-methoxy)benzoyl]aminoethyl [N6-benzoyl- 5'-O-(4,4'-dimethoxytrityl)-2'-deoxyadenosin-3'-yl]N,N-diisopropylphosphoramidite, 23

Compound 23 was synthesized analogously from N-benzoyl-5'-O-(4,4'-dimethoxytrityl)-2'-deoxyadenosine (6577 mg, 10.0 mmol), chloro bis[(N,N,-diisopropyl)amino] phosphite (3068 mg, 11.5 mmol) and N-(isopropyl)-N-[(4-methoxy)benzoyl]aminoethanol, 8, (2780 mg, 12.0 mmol). Column separation gave fast diastereomer 23f (970 mg), slow diastereomer 23s (1010 mg), and their mixture (6742 mg) totaled in 8722 mg (85.2%) of 23. $^{31}$P data are presented in Table 1

Fast diastereomer, 23f, $^1$H NMR (CDCl$_3$): 8.99 (1H, br. s.); 8.73 (1H, s); 8.20 (1H, s); 8.06–7.96 (2H, m); 7.65–7.45 (3H, m); 7.45–7.15 (11H, m); 6.9–6.7 (6H, m); 6.53 (1H, dd, J=6.2, 6.4 Hz); 4.77 (1H, m); 4.41 (1H, m); 3.80 (3H, s); 3.76 (6H, s); 4.2–3.3 (9H, m); 3.04–2.86 (1H, m); 2.72–2.57 (1H, m); 1.3–1.1 (18H, m). $^{13}$C NMR (CDCl$_3$) 171.91 (C=O); 164.67 [N$^6$—C (O)Ph]; 152.56 (C2); 151.53 (C6); 149.50 (C4); 142.25 (C8); 123.59 (C5); 86.52 (Ar$_3$C); 86.38 (C4'); 85.09 (C1'); 74.65, 73.35 (C3'); 63.56 (C5'); 61.45, 61.12 (P—O—CH$_2$); 55.33, 55.24 (OCH$_3$); 43.36, 42.93 (PN—CH); 39.64 (C2'); 24.78, 24.68 [P—N—C(CH)$_3$]; 21.20 [CN—C(CH)$_3$]; 160.44, 158.55, 144.58, 135.73, 133.81, 129.46 (Arom. C); 132.75, 130.08, 128.87, 128.23, 127.90, 126.92, 113.79, 113.17 (Arom. CH).

Slow diastereomer, 23s, $^1$H NMR (CDCl$_3$): 9.01 (1H, br. s.); 8.72 (1H, s); 8.18 (1H, s); 8.06–7.94 (2H, m); 7.65–7.45 (3H, m); 7.45–7.15 (l1H, m); 6.9–6.7 (6H, m); 6.54 (1H, dd, J=7.3, 6.4 Hz); 4.76 (1H, m); 4.32 (1H, m); 3.80 (3H, s); 3.76 (6H, s); 4.2–3.3 (9H, m); 3.04–2.84 (1H, m); 2.80–2.62 (1H, m); 1.3–1.05 (18H, m). $^{13}$C NMR (CDCl$_3$): 171.99 (C=O); 164.68 [N$^6$—C(O)Ph]; 152.51 (C2); 151.53 (C6); 149.49 (C4); 141.77 (C8); 123.59 (C5); 86.50 (Ar$_3$C); 86.11, 86.01 (C4'); 85.02 (C1'); 74.14, 73.76 (C3'); 63.60 (C5'); 61.34, 61.04 (P—O—CH$_2$); 55.33, 55.24 (OCH$_3$); 43.19, 42.95 (PN—CH); 39.43 (C2'); 24.73, 24.61 [P—N—C(CH)$_3$]; 21.23 [CN—C(CH$_3$)$_3$]; 160.44, 158.55, 144.55, 135.70, 133.81, 129.39 (Arom. C); 132.73, 130.07, 128.85, 128.21, 127.88, 127.74, 126.92, 113.80, 113.16 (Arom. CH).

Example 11

N-(Isopropyl)-N-[(4-methoxy)benzoyl]aminoethyl [N4-benzoyl-5'-O-(4,4'-dimethoxytrityl)-2'-deoxycytidin-3'-yl]N,N-diisopropylphosphoramidite, 24

Compound 24 was synthesized analogously from N4-benzoyl-5'-O-(4,4'-dimethoxytrityl)-2'-deoxycytidine (6177 mg, 10.0 mmol), chloro bis[(N,N,-diisopropyl)amino] phosphite (3068 mg, 11.5 mmol) and N-(isopropyl)-N-[(4-methoxy)benzoyl]aminoethanol, 8, (2780 mg, 12.0 mmol). Column separation gave fast diastereomer 24f (1184 mg), slow diastereomer 23s (1329 mg), and their mixture (5294 mg) totaled in 7808 mg (78.1%) of 24. $^{31}$P data are presented in Table 1.

Fast diastereomer, 24f, $^1$H NMR (CDCl$_3$): 8.56 (1H, br. s); 8.33 (1H, d, J=7.5 Hz); 7.88 (2H, m); 7.66–7.15 (15H, m); 6.90–6.74 (6H, m); 6.28 (1H, dd, J=5.9, 5.7 Hz); 4.67 (1H, m); 4.27 (1H, m); 3.79 (9H, s); 4.25–3.35 (9H, m); 2.79 (1H, m); 2.33 (1H, m); 1.30–1.10 (18H, m). $^{13}$C NMR (CDCl$_3$): 171.87 (C=O); 166.50 (C=O, N$^4$—Bz); 162.08 (C4); 154.77 (C2); 144.82 (C6); 96.37 (C5); 87.28 (C1'); 86.97 (Ar$_3$C); 86.20 (C4'); 71.85, 71.51 (C3'); 62.38 (C5'); 61.41, 61.15 (P—O—CH$_2$); 55.51 (CH$_3$O); 43.15, 42.92 (PN—CH); 41.21 (C2'); 24.76, 24.68 [P—N—C(CH$_3$)$_2$]; 21.30 [C—N—C(CH$_3$)$_2$]; 160.41, 158.71, 144.21, 135.58, 135.29, 133.29, 129.46 (Arom. C), 133.10, 130.20, 130.07, 128.23, 128.05, 127.57, 127.14, 113.78, 113.34 (Arom. CH).

Slow diastereomer, 24s, $^1$H NMR (CDCl$_3$): 8.64 (1H, br. s); 8.29 (1H, d, J=7.3 Hz); 7.88 (2H, m); 7.66–7.10 (15H, m); 6.92–6.80 (6H, m); 6.32 (1H, t, J=5.8 Hz); 4.62 (1H, m); 4.23 (1H, m); 3.80 (9H, s); 4.18–3.35 (9H, m); 2.81 (1H, m); 2.31 (1H, m); 1.30–1.0 (18H, m). $^{13}$C NMR (CDCl$_3$): 171.96 (C=O); 166.65 (C=O, N$^4$—Bz); 162.05 (C4); 154.70 (C2); 144.78 (C6); 96.42 (C5); 87.21 (C1'); 86.98 (Ar$_3$C); 86.01, 85.80 (C4'); 72.52, 72.16 (C3'); 62.51 (C5'); 61.18, 60.91 (P—O—CH$_2$); 55.26 (CH$_3$O); 43.14, 42.89 (PN—CH); 41.43 (C2'); 25.01, 24.87, 24.77, 24.51 [PN—C(CH$_3$)$_2$]; 21.20 [CN—C(CH$_3$)$_2$]; 160.4, 158.73, 144.14, 135.47, 135.26, 133.29, 129.47 (Arom. C), 133.11, 130.19, 129.03, 128.05, 127.57, 127.17, 113.80, 113.33 (Arom. CH).

Example 12

N-(Isopropyl)-N-[(4-methoxy)benzoyl]aminoethyl [N2-(isobutyryl)-5'-O-(4,4'-dimethoxytrityl)-2'-deoxyguanosin-3'-yl]N,N-diisopropylphosphoramidite, 25

Compound 25 was synthesized analogously from N2-isobutyryl-5'-O-(4,4'-dimethoxytrityl)-2'-deoxyguanosine (6397 mg, 10.0 mmol), chloro bis[(N,N,-diisopropyl)amino]phosphite (2935 mg, 11.0 mmol) and N-(isopropyl)-N-[(4-methoxy)benzoyl]aminoethanol, 8, (2780 mg, 12.0 mmol). Column separation gave fast diastereomer 25f (1010 mg), slow diastereomer 25s (457mg), and their mixture (5596 mg) totaled in 7063 mg (70.2%) of 25. $^{31}$P data are presented in Table 1.

Fast diastereomer, 25f, $^1$H NMR (CDCl$_3$): 7.78 (1H, s); 7.44–7.15 (13H, m); 6.94–6.74 (6H, m); 6.28 (1H, m); 4.56 (1H, m); 4.23 (1H, m); 3.78 (3H, s); 3.76 (6H, s); 4.15–3.20 (10H, m); 2.80–2.65 (1H, m); 2.43–2.25 (1H, m); 1.3–0.8 (24H, m). $^{13}$C NMR (CDCl$_3$): 179.93 (iPrC=O); 172.53 (AnC=O); 155.82 (C6); 148.19 (C2,C4); 121.31 (C5); 86.52 (Ar$_3$C); 85.83 (C1'); 84.53 (C4'); 74.15, 73.75 (C3'); 63.67 (C5'); 62.57, 62.40 (P—O—CH$_2$); 55.34, 55.22 (OCH$_3$); 43.26, 43.02 (P—N—CH); 40.85 (C2'); 35.45 [C(O)CH]; 24.75, 24.60, 24.45 [P—N—C(CH$_3$)$_2$]; 21.25 [C—N—C(CH$_3$)$_2$]; 18.90 [C(O)C(CH$_3$)$_2$]; 160.44, 158.62, 144.53, 135.58, 129.03 (Arom. C); 129.98, 128.02, 127.94, 127.63, 126.96, 113.89, 113.24 (Arom. CH).

Slow diastereomer, 25s, $^1$H NMR (CDCl$_3$): 7.77 (1H, s); 7.48–7.12 (13H, m); 6.90–6.70 (6H, m); 6.30 (1H, dd, J=7.7, 5.5 Hz); 4.67 (1H, m); 4.38 (1H, m); 3.76 (3H, s); 3.74 (6H, s); 4.15–3.18 (10H, m); 2.84–2.60 (1H, m); 2.53–2.35 (1H, m); 1.3–0.8 (24H, m). $^{13}$C NMR (CDCl$_3$): 179.44 (iPrC=O); 172.32 (AnC=O); 155.82 (C6); 148.52, 148.15 (C2,C4); 121.54 (C5); 86.44 (Ar$_3$C); 85.65, 85.53 (C4'); 84.12 (C1'); 73.78, 73.51 (C3'); 63.87 (C5'); 61–62 (br. m, P—O—CH$_2$); 55.33, 55.24 (OCH$_3$); 43.22, 43.98 (P—N—CH); 39.67 (C2'); 35.74 [C(O)CH]; 24.75, 24.61 [br. s, P—N—C(CH$_3$)$_2$]; 21.16 [C—N—C(CH$_3$)$_2$]; 18.86 [C(O)C(CH$_3$)$_2$]; 160.46, 158.63, 144.66, 135.71, 129.18 (Arom. C); 131.62, 130,04 128.12, 128.02, 127.95, 127.00, 113.85, 113.21 (Arom. CH).

Example 13

N-(Isopropyl)-N-[(4-methoxy)benzoyl]aminoethyl [5'-O-(4,4'-dimethoxytrityl)-2'-O-(2-methoxyethyl)-5-methyluridin-3'-yl]N,N-diisopropylphosphoramidite, 26

Compound 26 was synthesized analogously from 5'-O-(4,4'-dimethoxytrityl)-2'-O-(2-methoxyethyl)uridine (6027 mg, 10.0 mmol), chloro bis[(N,N,-diisopropyl)amino] phosphite (3068 mg, 11.5 mmol) and N-(isopropyl)-N-[(4-methoxy)benzoyl]aminoethanol, 8, (2780 mg, 12.0 mmol). Column separation gave fast diastereomer 26f (624 mg), slow diastereomer 26s (1745 mg), and their mixture (5702 mg) totaled in 8071 mg (81.9%) of 26. $^{31}$P and $^3$C NMR data are presented in Table 1 and Table 2, correspondingly.

Fast diastereomer, 26f, $^1$H NMR (CDCl$_3$): 8.53 (1H, br. s), 7.68 (1H, s); 7.50–7.20 (11H, m); 6.93–6.78 (6H, m); 6.05 (1H, d, J=4.8 Hz); 4.48 (1H, ddd, J=10.0, 4.5, 4.5 Hz); 4.31 (1H, m); 4.25 (2H, t, J=4.5 Hz), 3.81 (3H, s); 3.78 (6H, s); 3.33 (3H, s); 3.93–3.27 (12H, m); 1.33 (3H, s); 1.22–1.13 (12H, m); 1.08 (3H, d, J=7.3 Hz); 1.05 (3H, d, J=7.3 Hz).

Slow diastereomer, 26s, $^1$H NMR (CDCl$_3$): 8.15 (1H, br. s), 7.66 (1H, s); 7.45–7.20 (11H, m); 6.93–6.78 (6H, m); 6.08 (1H, d, J=5.0 Hz); 4.48 (1H, ddd, J=10.0, 4.5, 4.5 Hz); 4.27 (2H, t, J=4.9 Hz), 4.22 (1H, m); 3.82 (3H, s); 3.78 (6H, s); 3.32 (3H, s); 3.92–3.26 (12H, m); 1.31 (3H, s); 1.20–1.15 (12H, m); 1.01 (6H, d, J=6.7 Hz).

Example 14

N-Thiobenzoylaminoethyl [5'-O-(4,4'-dimethoxytrityl)thymidin-3'-yl]N,N-diisopropylphosphoramidite, 27

Compound 27 was synthesized analogously from 5'-O-(4,4'-dimethoxytrityl)thymidine (5446 mg, 10.0 mmol), chloro bis[(N,N,-diisopropyl)amino]phosphite (3068 mg, 11.5 mmol), and N-thiobenzoylaminoethanol, 9 (2139 mg, 11.8 mmol). Column separation gave fast diastereomer, 27f (460 mg), slow diastereomer, 27s (420 mg) and their mixture (4550 mg) to total in 5430 mg (63.5%) of 27. $^{31}$P and $^{13}$C NMR data are presented in Table 1 and Table 2, correspondingly.

Fast diastereomer, 27f, $^{1}$H NMR (CDCl$_3$): 9.3 (1H, br.s); 8.01 (1H, br.t); 7.76–7.54 (2H, m); 7.46–7.20 (13H, m); 6.86–6.76 (4H, m); 6.32 (1H, dd, J=6.5, 6.5 Hz); 4.65 (1H, m); 4.04 (1H, m); 4.0–3.85 (2H, m); 3.76 (6H, s); 3.71–3.36 (5H, m); 3.28 (1H, dd, J=2, 10.5 Hz); 2.39 (1H, m); 2.31 (1H, m); 1.41 (3H, s); 1.14 (12H, d, J=6.8 Hz).

Slow diastereomer, 27s, $^{1}$H NMR (CDCl$_3$): 9.4 (1H, br.s); 8.32 (1H, br.t); 7.76–7.68 (2H, m); 7.56 (1H, s); 7.44–7.20 (12H, m); 6.86–6.76 (4H, m); 6.36 (1H, dd, J=8.3, 5.5 Hz); 4.60 (1H, m); 4.14–4.0 (3H, m); 4.0–3.85 (1H, m); 3.77 (6H, s); 3.66–3.38 (3H, m); 3.28 (1H, dd, J=10.6, 2.4 Hz); 2.54 (1H, m); 2.21 (1H, m); 1.42 (3H, s); 1.13 (6H, d, J=6.6 Hz); 1.03 (6H, d, J=6.7 Hz).

Example 15

N-Thiobenzoylaminopropyl[5'-O-(4,4'-dimethoxytrityl)thymidin-3'-yl]N,N-diisopropylphosphoramidite, 28

Compound 28 was synthesized analogously from 5'-O-(4,4'-dimethoxytrityl)thymidine (1089 mg, 2.0 mmol), chloro bis[(N,N,-diisopropyl)amino]phosphite (587 mg, 2.2 mmol), and N-thiobenzoylaminoethanol, 10 (449 mg, 2.3 mmol). Column separation gave fast diastereomer, 28f (276 mg), slow diastereomer, 28s (296 mg) and their mixture (653 mg) to total in 1225 mg (70.5%) of 28. $^{31}$P and $^{13}$C NMR data are presented in Table 1 and Table 2, correspondingly.

Fast diastereomer, 28f, $^{1}$H NMR (CDCl$_3$): 8.36 (1H, br. t); 7.71–7.65 (2H, m); 7.61 (1H, d, J=1 Hz); 7.45–7.20 (13H, m); 6.86–6.78 (4H, m); 6.34 (1H, dd, J=7.3; 5.7 Hz); 4.62 (1H, m); 4.01 (1H, m); 3.78 (6H, s); 3.94–3.37 (7H, m); 3.23 (1H, dd, J=10.5, 2.6 Hz); 2.39 (1H, ddd, J=13.8, 5.7, 2.9 Hz); 2.26 (1H, ddd, J=13.8, 7.3, 6.9 Hz); 1.93 (2H, p, J=5.9); 1.41 (3H, s); 1.11 (6H, d, J=6.6 Hz); 1.08 (6H, d, J=6.6 Hz).

Slow diastereomer, 28s, $^{1}$H NMR (CDCl$_3$): 8.61 (1H, br. t); 7.8–7.7 (2H, m); 7.59 (1H, s); 7.45–7.20 (13H, m); 6.88–6.78 (4H, m); 6.37 (1H, dd, J=7.9; 5.5 Hz); 4.57 (1H, m); 4.06 (1H, m); 4.02–3.65 (4H, m); 3.56–3.34 (3H, m); 3.27 (1H, dd, J=10.3, 2.3 Hz); 2.48 (1H, dd, J=13.4, 5.5 Hz); 2.23 (1H, ddd, J=13.4, 7.9, 5.6 Hz); 2.08 (2H, m); 1.42 (3H, s); 1.09 (6H, d, J=6.8 Hz); 0.99 (6H, d, J=6.5 Hz).

Example 16

N-[(N-Phenyl)thiocarbamoyl]aminoethyl[5'-O-(4,4'-dimethoxytrityl)thymidin-3'-yl]N,N-diisopropylphosphoramaidite, 29

Compound 29 was synthesized analogously from 5'-O-(4,4'-dimethoxytrityl)thymidine (1089 mg, 2.0 mmol), chloro bis[(N,N,-diisopropyl)amino]phosphite (587 mg, 2.2 mmol), and N-[(N-phenyl)thiocarbamoyl]aminoethanol, 11 (451 mg, 2.3 mmol). Column separation gave fast diastereomer, 29f (134 mg), slow diastereomer, 29s (395 mg) and their mixture (697 mg) to total in 1226 mg (70.5%) of 29. $^{31}$P and $^{13}$C NMR data are presented in Table 1 and Table 2, correspondingly.

Fast diastereomer, 29f, $^{1}$H NMR (CDCl$_3$): 8.10 (1H, br. s); 7.64 (1H, s); 7.42–7.14 (15H, m); 6.88–6.78 (4H, m); 6.42–6.32 (2H, m); 4.55 (1H, m); 4.02 (1H, m); 3.79 (6H, s); 3.90–3.64 (2H, m); 3.63–3.53 (2H, m); 3.50–3.30 (3H, m); 3.22 (1H, dd, J=10.6, 2.4 Hz); 2.40 (1H, ddd, J=13.7, 6.1, 2.5 Hz); 2.25 (1H, ddd, J=13.7, 7.3, 6.4 Hz); 1.40 (3H, s); 1.09 (6H, d, J=6.8 Hz); 1.03 (6H, d, J=6.8 Hz).

Slow diastereomer, 29s, $^{1}$H NMR (CDCl$_3$): 8.51 (1H, br. s); 7.60 (1H, d, J=1 Hz); 7.42–7.16 (15H, m); 6.88–6.78 (4H, m); 6.60 (1H, br. t); 6.37 (1H, dd, J=8.3, 5.6 Hz); 4.57 (1H, m); 4.05 (1H, m); 3.78 (6H, s); 3.90–3.20 (8H, m); 2.48 (1H, dd, J=13.3, 5.6 Hz); 2.22 (1H, ddd, J=13.3, 8.3, 5.9 Hz); 1.42 (3H, s); 1.03 (6H, d, J=6.7 Hz); 0.98 (6H, d, J=6.7 Hz).

Example 17

O-[N-(Naphthyl-1)carbamoyl]oxyethyl[5'-O-(4,4'-dimethoxytrityl)thymidin-3'-yl]N,N-diisopropylphosphoramidite, 32

Compound 32 was synthesized analogously from 5'-O-(4,4'-dimethoxytrityl)thymidine (2178 mg, 4.0 mmol), chloro bis[(N,N,-diisopropyl)amino]phosphite (1280 mg, 4.8 mmol), and N-[(N-phenyl)thiocarbamoyl]aminoethanol, 14 (1110 mg, 4.8 mmol). Column separation gave fast diastereomer, 32f (514 mg), slow diastereomer, 32s (452 mg), and their mixture (2249 mg) to total in 3215 mg (88.8%) of 32. $^{31}$P data are presented in Table 1.

Fast diastereomer, 32f, $^{1}$H NMR (CDCl$_3$): 8.89 (1H, br. s); 7.92–7.20 (17H, m); 7.07 (1H, s); 6.84–6.76 (4H, m); 6.42 (1H, m); 4.71 (1H, m); 4.45–4.16 (3H, m); 3.75 (6H, s); 3.90–3.30 (6H, m); 2.55 (1H, m); 2.36 (1H, m); 1.42 (3H, s); 1.19 (12H, d, J=5.5 Hz). $^{13}$C NMR (CDCl$_3$): 163.86 (C4), 154.29 (C=O), 150.37 (C2), 135.72 (C6), 111.18 (C5), 86.93 (Ar$_3$C), 85.92, 85.77 (C4'), 84.94 (C1'), 73.60, 73.27 (C3'), 65.40, 65.26 (P—O—C—CH$_2$), 63.15 (C5'), 61.80, 61.47 (P—O—CH$_2$), 55.27 (CH$_3$O), 43.32, 43.08 (N—CH), 40.12 (C2'), 24.70, 24.57 (N—C—CH$_3$), 11.77 (C5-CH$_3$), Arom.: 158.73 (C), 144.43 (C), 135.46 (C), 134.09 (C), 132.50 (C), 130.16 (CH), 128.67 (CH), 128.20 (CH), 128.03 (CH), 127.69 (C), 127.17 (CH), 126.20 (CH), 126.05 (CH), 125.77 (CH), 125.17 (CH) 120.66 (CH), 113.30 (CH).

Slow diastereomer, 32s, $^{1}$H NMR (CDCl$_3$): 7.94–7.76 (3H, m); 7.70–7.18 (16H, m); 6.88–6.76 (4H, m); 6.42 (1H, dd, J=7.9, 5.9 Hz); 4.67 (1H, m); 4.50–4.15 (3H, m); 3.77 (6H, s); 4.0–3.25 (8H, m); 2.63 (1H, ddd, J=13.5, 4.0, ≈1 Hz); 2.32 (1H, m); 1.41 (3H, s); 1.17 (6H, d, J=6.8 Hz); 1.08 (6H, d, J=6.8 Hz). $^{13}$C NMR (CDCl$_3$): 163.74 (C4), 154.51 (C=O), 150.43 (C2), 135.67 (C6), 111.21 (C5), 86.93 (Ar$_3$C), 85.67, 85.54 (C4'), 85.01 (C1'), 74.14, 73.78 (C3'), 65.40, 65.25 (P—O—C—CH$_2$), 63.43 (C5'), 61.84, 61.51 (P—O—CH$_2$), 55.28 (CH$_3$O), 43.25, 43.00 (N—CH), 40.12 (C2'), 24.67, 24.54 (N—C—CH$_3$), 11.80 (C5-CH$_3$), Arom.: 158.75 (C), 144.36 (C), 135.47 (C), 135.37 (C), 134.11 (C), 132.67 (C), 130.14 (CH), 128.65 (CH), 128.19 (CH), 128.03 (CH), 127.69 (C), 127.17 (CH), 126.02 (CH), 125.77 (CH), 125.18 (CH), 120.94 (CH), 113.31 (CH).

The compounds of the present invention may be further understood by reference to the following tables.

TABLE 1

Table 1 provides the acylaminoalcohols 1–8 of general formula I-a:

I-a

| Compound | Formula | R¹ | R² | R³ |
|---|---|---|---|---|
| 1 | I-a | H | H | H |
| 2 | I-a | 3-NO₂ | H | H |
| 3 | I-a | 4-MeO | H | H |
| 4 | I-a | H | H | Me |
| 5 | I-a | H | Me | H |
| 6 | I-a | 4-MeO | Me | H |
| 7 | I-a | 4-Me₂N | Me | H |
| 8 | I-a | 4-MeO | iPr | H |

TABLE 2

Table 2 provides phosphoroamidites 15–26 of general formula II-a:

II-a

| Compound | R | Base | R¹ | R² | R³ |
|---|---|---|---|---|---|
| 15 | H | T | H | H | H |
| 16 | H | T | 3-NO₂ | H | H |
| 17 | H | T | 4-MeO | H | H |
| 18 | H | T | H | H | Me |
| 19 | H | T | H | Me | H |
| 20 | H | T | 4-MeO | Me | H |
| 21 | H | T | 4-Me₂N | Me | H |
| 22 | H | T | 4-MeO | iPr | H |
| 23 | H | A$^{bz}$ | 4-MeO | iPr | H |
| 24 | H | C$^{bz}$ | 4-MeO | iPr | H |
| 25 | H | G$^{ib}$ | 4-MeO | ipr | H |
| 26 | *MOE | T | 4-MeO | iPr | H |

*MOE = (2-methoxyethyl) oxy

TABLE 3

Table 3 provides thioacylaminoalkohols 9–11 of general formula I-b:

I-b

| Compound | n | R¹ | Z |
|---|---|---|---|
| 9 | 1 | H | a bond |
| 10 | 2 | H | a bond |
| 11 | 1 | H | —NH— |

TABLE 4

Table 4 provides phosphoroamidites 27–29 of general formula II-b:

II-b

| Compound | n | R | Base | R¹ | Z |
|---|---|---|---|---|---|
| 27 | 1 | H | T | H | a bond |
| 28 | 2 | H | T | H | a bond |
| 29 | 1 | H | T | H | —NH— |

TABLE 5

Table 3 provides (2-hydroxyethyl)N-arylcarbamates 12–14 of general formula I-c:

I-c

| Compound | R |
|---|---|
| 12 | Ph |
| 13 | C₆H₄-(4-Me₂N) |
| 14 | 1-naphthyl |

TABLE 6

Table 6 provides phosphoroamidites 30–32 of general formula II-c:

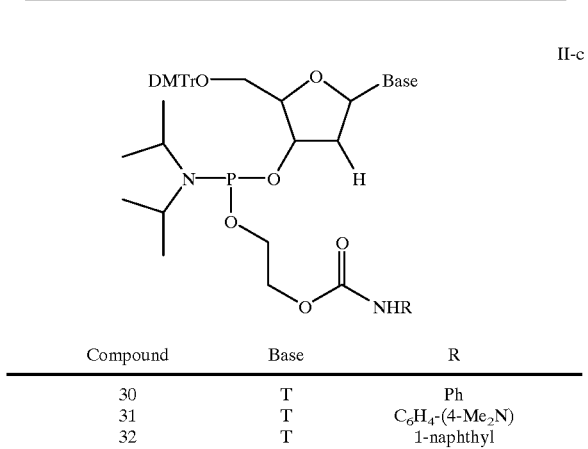

| Compound | Base | R |
|---|---|---|
| 30 | T | Ph |
| 31 | T | $C_6H_4$-(4-$Me_2N$) |
| 32 | T | 1-naphthyl |

Example 18
General Oligonucleotide Synthesis Conditions

The oligonucleotide synthesis was performed on an ABI 380B DNA Synthesizer. To check the efficiency of removal of protecting groups, a solid support bound DMT-$T_{12}$ was assembled using phosphoramidites 15–22 and 27–32 (0.1 M in MeCN), standard ancillary reagents, cycles, and procedures. Following the coupling with compounds 15–26 and 30–32, a commercial oxidizer was used. For 27–29, the oxidation step was performed with the aid of t-butyl hydroperoxide (10% in MeCN). For preparation of phosphorothioate oligonucleotides, 3H-1,2-benzodithiol-3-one 1,1-dioxide (0.05 M in MeCN) was employed as the sulfur-transfer reagent. In all cases coupling yields greater than 98% were observed. Solid support bound oligonucleotides were deprotected using the conditions specified in the Table 7.

TABLE 7

| Phosphormidite | Backbone | Agent | Time | Temp. |
|---|---|---|---|---|
| 15 | P=O | Conc. $NH_3/H_2O$ | 48 | 55 |
| 16 | P=O | Conc. $NH_3/H_2O$ | 48 | 55 |
| 17 | P=O | Conc. $NH_3/H_2O$ | 48 | 55 |
| 18 | P=O | Conc. $NH_3/H_2O$ | 8 | 55 |
| 19 | P=O | Conc. $NH_3/H_2O$ | 6 | 55 |
| 20 | P=O | Conc. $NH_3/H_2O$ | 5 | 55 |
| 21 | P=O | Conc. $NH_3/H_2O$ | 6 | 25 |
| 22–26 | P=O | Conc. $NH_3/H_2O$ | 0.5 | 25 |
| 22–26 | P=S | Conc. $NH_3/H_2O$ | 0.5 | 25 |
| 27 | P=O | Conc. $NH_3/H_2O$ | 1 | 25 |
| 27 | P=O | 0.01M $K_2CO_3$/MeOH | 8 | 25 |
| 27 | P=S | Conc. $NH_3/H_2O$ | 1.5 | 25 |
| 28 | P=O | Conc. $NH_3/H_2O$ | 1.5 | 25 |
| 28 | P=S | Conc. $NH_3/H_2O$ | 1.5 | 25 |
| 29 | P=O | Conc. $NH_3/H_2O$ | 1.5 | 25 |
| 29 | P=O | 0.01M $K_2CO_3$/MeOH | 8 | 25 |
| 29 | P=S | Conc. $NH_3/H_2O$ | 1 | 25 |
| 32 | P=O | Conc. $NH_3/H_2O$ | 6 | 25 |

The deprotection mixtures of Table 7 were evaporated to dryness, dissolved in water, and analyzed by HPLC.

HPLC Conditions

Crude oligonucleotides were analyzed on a DeltaPak 15m C18 300 HPLC column (3.8' 300 mm) eluted with a linear gradient from 0 to 60% B in 40 min (0.1 M aq $NH_4OAc$ as buffer A, 80% aq MeCN as buffer B). Authentic DMTr-$T_{12}$ and DMTr-$T_{12}$ phosphorothioate synthesized by routine methods were used as reference samples.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for the preparation of an oligomeric compound comprising a moiety of Formula X:

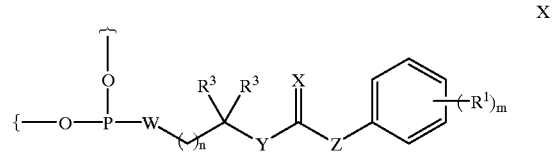

wherein:

W is selected independently from O and S;

X is selected independently from O and S;

Y is selected independently from O and $NR^2$;

Z is selected independently from a single bond, O, and $NR^2$;

$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl; alternatively, two $R^1$ groups, when on adjacent carbons of the phenyl ring, join to form a napthyl ring that includes said phenyl ring;

$R^2$, at each occurrence, is selected independently from H, $C_{1-6}$ alkyl, $C_{2-6}$ alkenyl, $C_{2-6}$ alkynyl, $C_{3-6}$ cycloalkyl, and phenyl;

$R^3$, at each occurrence, is selected independently from hydrogen, $C_{1-6}$ alkyl, $C_{2-6}$ alkenyl, $C_{2-6}$ alkynyl, $C_{3-6}$ cycloalkyl, and phenyl;

$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;

n is selected independently from 0, 1, 2, and 3; and m is selected independently from 0, 1, 2, and 3;

the method comprising:

(a) providing a compound of Formula II:

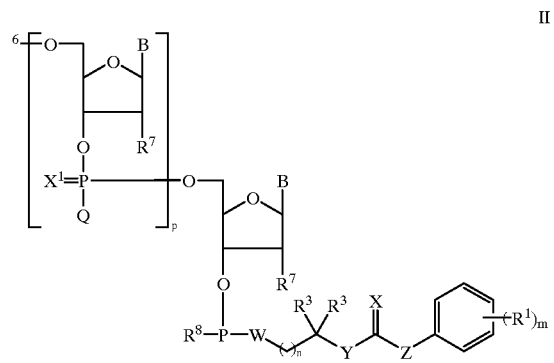

wherein:

R$^6$, at each occurrence, is selected independently from H, a hydroxyl protecting group, and a linker connected to a solid support;

R$^7$, at each occurrence, is indepedently H, hydroxyl, C$_{1-20}$ alkyl, C$_{3-20}$ alkenyl, C$_{2-20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, dilulfide, silyl, aryl, heterocycle, carbocycle, intercalator, reporter molecule, conjugate, polyamine, polyamide, polyalkylene glycol, polyether, or one of formula XII or XIII:

$$-\!\!\left[\mathrm{O}-(\mathrm{CH_2})_{q1}\right]_{q2}\!\!\!-\!(\mathrm{O})_{q3}\!-\!\mathrm{E} \quad \mathrm{XII}$$

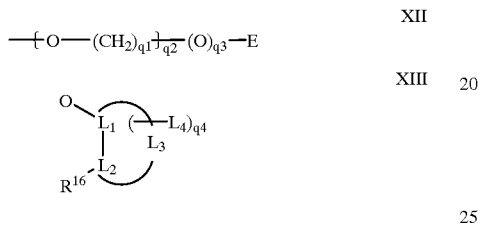

XIII wherein

E is selected from C$_{1-10}$ alkyl, N(R$^{15}$)(R$^{17}$) and N=C(R$^{15}$)(R$^{17}$);

R$^{15}$ and R$^{17}$ are independently selected from H, C$_{1-10}$ alkyl, dialkylaminoalkyl, a nitrogen protecting group, a tethered or untethered conjugate group, a linker to a solid support, or alternatively R$^{15}$ and R$^{17}$, together, are joined in a nitrogen protecting group or a ring structure that can include at least one additional heteroatom selected from N and O;

q$^1$ is from 1 to 10;

q$^2$ is from 1 to 10;

q$^3$ is 0 or 1;

R$^{16}$ is OR$^{18}$, SR$^{18}$, or N(R$^{18}$)$_2$;

R$^{18}$ is selected independently from H, C$_1$–C$_8$ alkyl, C$_1$–C$_8$ haloalkyl, C(=NH)N(H)R$^{19}$, C(=O)N(H)R$^{19}$ and OC(=O)N(H)R$^{19}$;

R$^{19}$ is H or C$_1$–C$_8$ alkyl;

L$_1$, L$_2$ and L$_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

L$_4$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$^{15}$)(R$^{17}$) OR$^{15}$, halo, SR$^{15}$ or CN; and q$^4$ is, 0, 1 or 2;

R$^8$ is selected independently from NR$^{8a}$R$^{8b}$, and a 5–6 membered heterocyclic system containing 1–4 heteroatoms selected independently from N, O, and S;

R$^{8a}$ and R$^{8b}$, at each occurrence, are selected independently from C$_{1-10}$ alkyl and C$_{3-7}$ cycloalkyl;

X$^1$ is selected independently from O and S;

B, at each occurrence, is independently selected from a protected or unprotected naturally occurring nucleobase, and a protected or unprotected non-naturally occurring nucleobase;

q is selected independently from 1, 2, 3, 4, 5, 6, 7, 8, 9, and 10;

p is an integer selected independently from 0 to about 50;

Q, at each occurrence, is selected independently from OH, SH, and

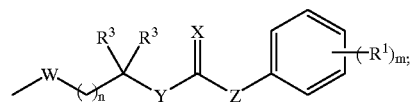

(b) reacting the compound of Formula II with a compound of Formula III:

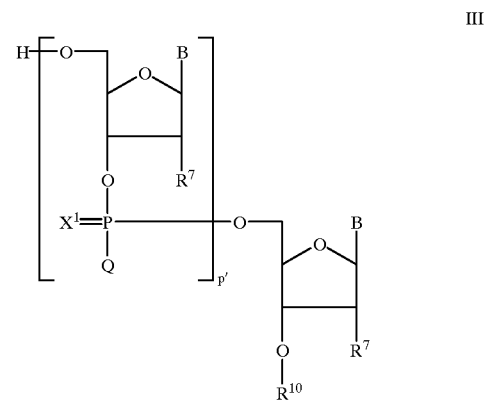

wherein

R$^{10}$ is selected independently from a hydroxyl protecting group, and a linker connected to a solid support;

with the proviso that R$^6$ and R$^{10}$ are not both simultaneously a linker connected to a solid support; and p' is an integer selected independently from 0 to about 50; to form the oligomeric compound.

2. The method of claim 1, further comprising treating said oligomeric compound with a reagent under conditions of time temperature and pressure effective to oxidize or sulfurize the oligomeric compound.

3. The method of claim 2 wherein R$^{10}$ is a linker connected to a solid support, further comprising treating the oligomeric compound with a reagent under conditions of time temperature and pressure effective to deprotect the oligomeric compound.

4. The method of claim 3 wherein the deprotection is effective to remove the oligomeric compound from the solid support.

5. The method of claim 3 further comprising treating the oligomeric compound with a reagent under conditions of time temperature and pressure effective to remove the oligomeric compound from the solid support.

6. The method of claim 1, wherein R$^1$ is selected independently from CH$_3$, CH$_2$CH$_3$, CH(CH$_3$)$_2$, CN, NO$_2$, OCH$_3$, OCH$_2$CH$_3$, OCH(CH$_3$)$_2$, N(CH$_3$)$_2$, N(CH$_2$CH$_3$)$_2$, and N(CH(CH$_3$)$_2$)$_2$; R$^2$ is selected independently from H and C$_{1-3}$ alkyl; R$^3$ is H; Y is N—R$^2$; Z is said bond; n is 1; and m is selected independently from 0 and 1.

7. The method of claim 6, wherein m is 1, R$^1$ is OCH$_3$, and is in the para position.

8. The method of claim 7, wherein each R$^{8a}$ and R$^{8b}$ are isopropyl.

9. The method of claim 7 wherein $X^1$ is O.
10. The method of claim 7 wherein $X_1$ is S.
11. The method of claim 9 wherein W is S.
12. The method of claim 9 wherein W is O.
13. The method of claim 10 wherein W is S.
14. The method of claim 1, wherein the compound of Formula II is obtained by reaction of a compound of Formula V:

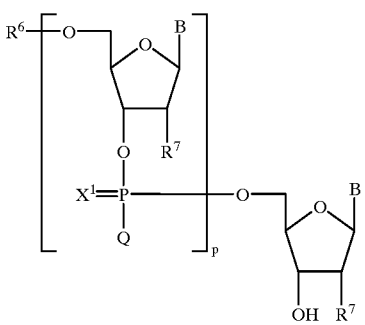

with a compound of Formula VI:

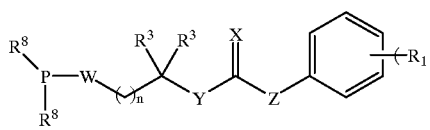

in the presence of an acid.

15. The method of claim 1, wherein the compound of Formula II is obtained by reaction of a compound of Formula V:

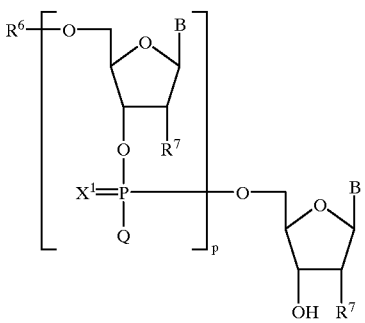

with a chlorophosphine compound of formula ClP(NR$^{8a}$R$^{8b}$)$_2$, followed by reaction with a compound of Formula I-i:

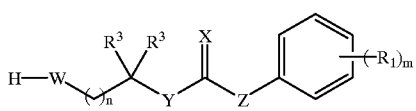

in the presence of an acid.

16. The method of claim 15, wherein W is O; Z is selected independently from a single bond and NR$^2$; R$^1$ is selected independently from CH$_3$, CH$_2$CH$_3$, CH(CH$_3$)$_2$, CN, NO$_2$, OCH$_3$, OCH$_2$CH$_3$, OCH(CH$_3$)$_2$, N(CH$_3$)$_2$, N(CH$_2$CH$_3$)$_2$, and N(CH(CH$_3$)$_2$)$_2$;

R$^3$ is selected independently from H and CH$_3$;
R$^4$ are H;
n is selected independently from 1 and 2; and
m is selected independently from 0 and 1.

17. A method for the preparation of a compound of Formula II:

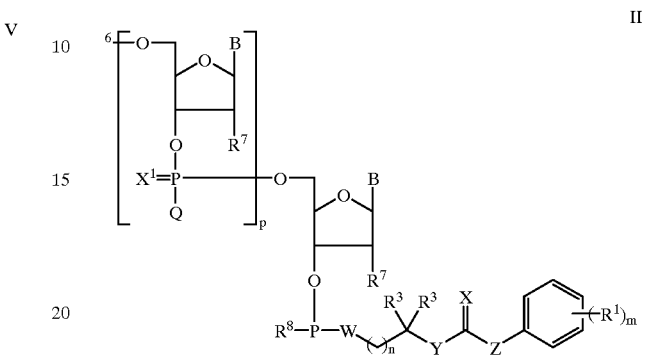

wherein:

W is selected independently from O and S;

X is selected independently from O and S;

Y is selected independently from O and NR$^2$;

Z is selected independently from a single bond, O, and NR$^2$;

R$^1$, at each occurrence, is selected independently from C$_{1-6}$ alkyl, C$_{2-6}$ alkenyl, C$_{2-6}$ alkynyl, C$_{3-6}$ cycloalkyl, CN, NO$_2$, Cl, Br, F, I, CF$_3$, OR$^4$, NR$^{5a}$R$^{5b}$, and phenyl;

alternatively, two R$^1$ groups, when on adjacent carbons of the phenyl ring, join to form a napthyl ring that includes said phenyl ring;

R$^2$, at each occurrence, is selected independently from H, C$_{1-6}$ alkyl, C$_{2-6}$ alkenyl, C$_{2-6}$ alkynyl, C$_{3-6}$ cycloalkyl, and phenyl;

R$^3$, at each occurrence, is selected independently from hydrogen, C$_{1-6}$ alkyl, C$_{2-6}$ alkenyl, C$_{2-6}$ alkynyl, C$_{3-6}$ cycloalkyl, and phenyl;

R$^4$ is selected independently from C$_{1-6}$ alkyl, C$_{3-6}$ cycloalkyl, and phenyl;

R$^{5a}$ and R$^{5b}$, at each occurrence, are selected independently from C$_{1-6}$ alkyl, C$_{3-6}$ cycloalkyl, and phenyl;

n is selected independently from 0, 1, 2, and 3; and m is selected independently from 0, 1, 2, and 3;

R$^6$, at each occurrence, is selected independently from H, a hydroxyl protecting group, and a linker connected to a solid support;

R$^7$, at each occurrence, is indepedently H, hydroxyl, C$_1$–C$_{20}$ alkyl, C$_3$–C$_{20}$ alkenyl, C$_2$–C$_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, dilulfide, silyl, aryl, heterocycle, carbocycle, intercalator, reporter molecule, conjugate, polyamine, polyamide, polyalkylene glycol, polyether, or one of formula XII or XIII:

$$-\!\!+\!\!\text{O}-\!\!(\text{CH}_2)_{q1}\!\!+\!\!_{q2}\!\!-\!\!(\text{O})_{q3}\!\!-\!\!\text{E} \qquad \text{XII}$$

[Structure XIII with L1, L2, L3, L4, R16]

wherein

E is selected from $C_1$–$C_{10}$ alkyl, $N(R^{15})(R^{17})$ and $N\!\!=\!\!C(R^{15})(R^{17})$;

$R^{15}$ and $R^{17}$ is independently selected from H, $C_1$–$C_{10}$ alkyl, dialkylaminoalkyl, a nitrogen protecting group, a tethered or untethered conjugate group, a linker to a solid support, or alternatively $R^{15}$ and $R^{17}$, together, are joined in a nitrogen protecting group or a ring structure that can include at least one additional heteroatom selected from N and O;

$q^1$ is from 1 to 10;

$q^2$ is from 1 to 10;

$q^3$ is 0 or 1;

$R^{16}$ is $OR^{18}$, $SR^{18}$, or $N(R^{18})_2$;

$R^{18}$ is selected independently from H, $C_1$–$C_8$ alkyl, $C_1$–$C_8$ haloalkyl, $C(\!\!=\!\!NH)N(H)R^{19}$, $C(\!\!=\!\!O)N(H)R^{19}$ and $OC(\!\!=\!\!O)N(H)R^{19}$;

$R^{19}$ is H or $C_1$–$C_8$ alkyl;

$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$L_4$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R^{15})(R^{17})$ $OR^{15}$, halo, $SR^{15}$ or CN; and $q^4$ is, 0, 1 or 2;

$R^8$ is selected independently from $NR^{8a}R^{8b}$, and a 5–6 membered heterocyclic system containing 1–4 heteroatoms selected independently from N, O, and S;

$R^{8a}$ and $R^{8b}$, at each occurrence, are selected independently from $C_{1-10}$ alkyl and $C_{3-7}$ cycloalkyl;

$X^1$ is selected independently from O and S;

B, at each occurrence, is independently selected from a protected or unprotected naturally occurring nucleobase, and a protected or unprotected non-naturally occurring nucleobase;

q is selected independently from 1, 2, 3, 4, 5, 6, 7, 8, 9, and 10;

p is an integer selected independently from 0 to about 50;

Q, at each occurrence, is selected independently from SH, OH, and

[Structure with $R^3$, $R^3$, X, W, Y, Z, $(R^1)_m$]

the method comprising:

reacting a nucleoside of Formula V:

[Formula V with $R^6$, B, $R^7$, $X^1$, P, Q, OH, $R^7$]

with a chlorophosphine compound of formula $ClP\!\!-\!\!(R^8)_2$, in the presence of a base; and protecting the product by reaction with a compound of Formula I-i:

I-i

[Structure I-i with H—W, $R^3$, $R^3$, X, Y, Z, $(R^1)_m$]

in the presence of an acid to form the compound of Formula II.

18. The method of claim 17, wherein $R^1$ is in the meta or para position and is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$; $R^2$ is selected independently from $CH_3$, $CH_2CH_3$, and $CH(CH_3)_2$; $R^3$ is selected independently from H and $CH_3$; n is selected independently from 1 and 2; and m is selected independently from 0 and 1.

19. The method of claim 18 wherein W is O.

20. The method of claim 19 wherein $R^8$ is $NR^{8a}R^{8b}$, and $R^{8a}$ and $R^{8b}$ are each isopropyl.

21. The method of claim 19 wherein p is 0.

22. The method of claim 19 wherein p is 0.

23. A compound of Formula I:

I

[Structure I with *—W, $R^3$, $R^3$, X, Y, Z, $(R^1)_m$]

wherein:

* indicates the point of attachment to the phosphorus atom of an oligomeric compound;

W is selected independently from O and S;

X is selected independently from O and S;

Y is selected independently from O and $NR^2$;

Z is selected independently from a single bond, O, and $NR^2$;

$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl; alternatively, two $R^1$ groups, when on adjacent carbons of the phenyl ring, join to form a napthyl ring that includes said phenyl ring;

$R^2$, at each occurrence, is selected independently from H, $C_{1-6}$ alkyl, $C_{2-6}$ alkenyl, $C_{2-6}$ alkynyl, $C_{3-6}$ cycloalkyl, and phenyl;

$R^3$, at each occurrence, is selected independently from hydrogen, $C_{1-6}$ alkyl, $C_{2-6}$ alkenyl, $C_{2-6}$ alkynyl, $C_{3-6}$ cycloalkyl, and phenyl;

$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;

n is selected independently from 0 to about 3; and m is selected independently from 0 to about 3.

24. The compound of claim 23, wherein $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$.

25. The compound of claim 24 wherein each $R^3$ is hydrogen, Y is $NR^2$, and Z is a single bond.

26. The compound of claim 25, wherein $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$.

27. The compound of claim 28, wherein $R^2$ is selected independently from H, $CH_3$, $CH_2CH_3$, and $CH(CH_3)_2$; n is selected independently from 1 and 2; and m is selected independently from 0 and 1.

28. The compound of claim 23 wherein each $R^3$ is hydrogen and Z is $NR^2$.

29. The compound of claim 28, wherein each $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$.

30. The compound of claim 29, wherein $R^2$ is H; n is selected independently from 1 and 2; and m is selected independently from 0 and 1.

31. A compound of Formula VII:

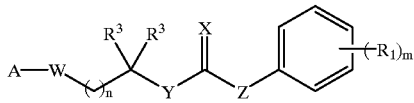

VII wherein:

W is selected independently from O and S;

X is selected independently from O and S;

Y is selected independently from O and $NR^2$;

Z is selected independently from a single bond, O, and $NR^2$;

$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl;

alternatively, two $R^1$ groups, when on adjacent carbons of the phenyl ring, join to form a napthyl ring that includes said phenyl ring;

$R^2$, at each occurrence, is selected independently from H, $C_{1-6}$ alkyl, $C_{2-6}$ alkenyl, $C_{2-6}$ alkynyl, $C_{3-6}$ cycloalkyl and phenyl;

$R^3$, at each occurrence, is selected independently from hydrogen, $C_{1-6}$ alkyl, $C_{2-6}$ alkenyl, $C_{2-6}$ alkynyl, $C_{3-6}$ cycloalkyl, and phenyl;

$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;

n is selected independently from 0, 1, 2, and 3;

m is selected independently from 0, 1, 2, and 3;

A is selected independently from $(R^8)_2P$, $R^8R^{11}P$, $R^8R^{12}P$, and $R^{11}R^{12}P$;

$R^8$ is selected independently from $NR^{8a}R^{8b}$, and a 5–6 membered heterocyclic system containing 1–4 heteroatoms selected independently from N, O, and S;

$R^{8a}$ and $R^{8b}$, at each occurrence, are selected independently from $C_{1-10}$ alkyl and $C_{3-7}$ cycloalkyl;

$R^{11}$ is a compound of Formula VIII:

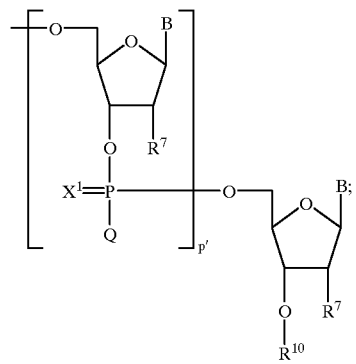

VIII $R^7$, at each occurrence, is indepedently H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, dilulfide, silyl, aryl, heterocycle, carbocycle, intercalator, reporter molecule, conjugate, polyamine, polyamide, polyalkylene glycol, polyether, or one of formula XII or XIII:

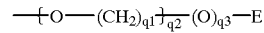

XII

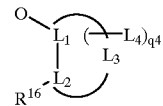

XIII wherein

E is selected from $C_1$–$C_{10}$ alkyl, $N(R^{15})(R^{17})$ and $N=C(R^{15})(R^{17})$;

$R^{15}$ and $R^{17}$ is independently selected from H, $C_1$–$C_{10}$ alkyl, dialkylaminoalkyl, a nitrogen protecting group, a tethered or untethered conjugate group, a linker to a solid support, or alternatively $R^{15}$ and $R^{17}$, together, are joined in a nitrogen protecting group or a ring structure that can include at least one additional heteroatom selected from N and O;

$q^1$ is from 1 to 10;

$q^2$ is from 1 to 10;

$q^3$ is 0 or 1;

$R^{16}$ is $OR^{18}$, $SR^{18}$, or $N(R^{18})_2$;

$R^{18}$ is selected independently from H, $C_1$–$C_8$ alkyl, $C_1$–$C_8$ haloalkyl, $C(=NH)N(H)R^{19}$, $C(=O)N(H)R^{19}$ and $OC(=O)N(H)R^{19}$;

$R^{19}$ is H or $C_1$–$C_8$ alkyl;

$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

$L_4$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R^{15})(R^{17})$, $OR^{15}$, halo, $SR^{15}$ or CN; and $q^4$ is, 0, 1 or 2;

$X^1$ is selected independently from O and S;

B, at each occurrence, is independently selected from a protected or unprotected naturally occurring nucleobase, and a protected or unprotected non-naturally occurring nucleobase;

$R^{10}$ is selected independently from H, a hydroxyl protecting group, and a linker connected to a solid support;

p' is an integer selected independently from 0 to about 50;

Q, at each occurrence, is selected independently from SH, OH and

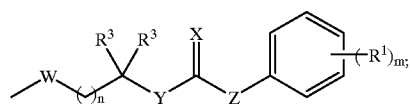

$R^{12}$ is a compound of Formula IX:

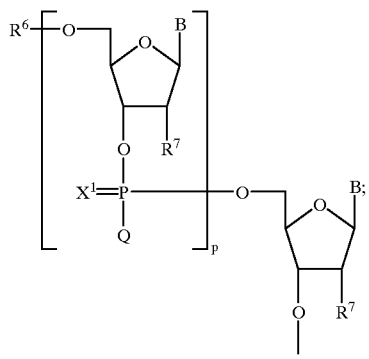

wherein:

$R^6$ is selected independently from H, a hydroxyl protecting group, and a linker connected to a solid support; and p is an integer selected independently from 0 to about 50;

with the provisos that the sum of p and p' does not exceed 50, and when A is $PR^{11}R^{12}$, $R^6$ and $R^{10}$ are not both simultaneously a linker connected to a solid support.

32. The compound of to claim 31, wherein $R^3$ is hydrogen, Y is $NR^2$, and Z is said single bond.

33. The compound of claim 32, wherein m is 1, and $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$.

34. The compound of claim 32 wherein W is O.

35. The compound of claim 31, wherein each $R^3$ is hydrogen and Z is $NR^2$.

36. The compound of claim 35 wherein m is 1, and $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$.

37. The compound of claim 35 wherein W is O.

38. The compound of claim 35 wherein W is S.

39. The compound of claim 31 wherein A is $P(R^8)_2$.

40. The compound of claim 39 wherein $R^8$ is $N(CH(CH_3)_2)_2$.

41. The compound of claim 31 wherein A is $PR^{12}R^8$.

42. The compound of claim 41 wherein p is 0.

43. The compound of claim 42 wherein $R^6$ is a hydroxyl protecting group.

44. The compound of claim 43 wherein Y is $NR^2$, $R^2$ is selected independently from H, $CH_3$, $CH_2CH_3$, and $CH(CH_3)_2$; n is selected independently from 1 and 2; m is selected independently from 0 and 1, and $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$.

45. The compound of claim 31 wherein A is $PR^{11}R^8$.

46. The compound of claim 31, wherein the compound of Formula VII is:

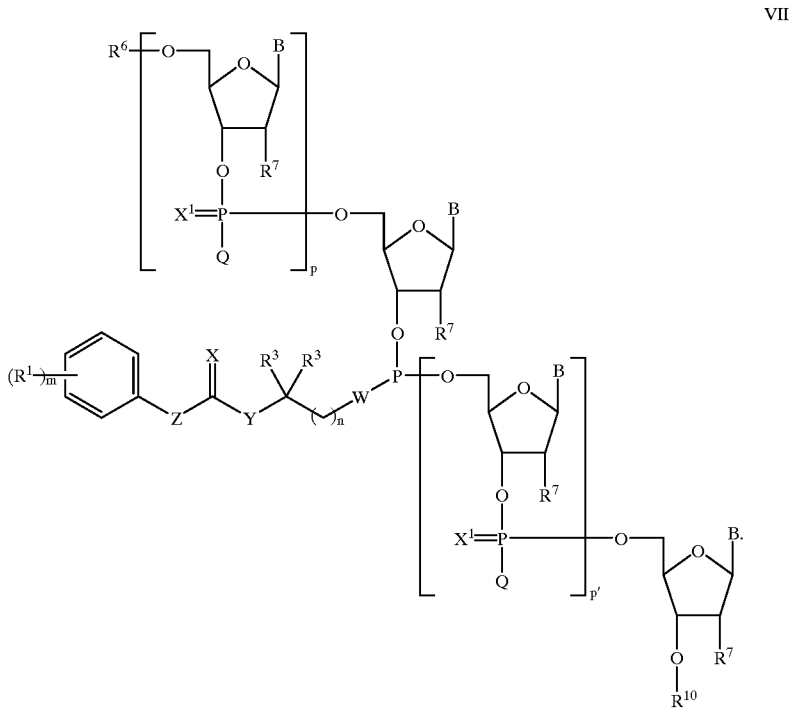

47. The compound of claim 46, wherein Y is $NR^2$; $R^2$ is selected independently from H, $CH_3$, $CH_2CH_3$, and $CH(CH_3)_2$; n is selected independently from 1 and 2; and m is selected independently from 0 and 1.

48. The compound of claim 46 wherein $R^{10}$ is a linker connected to a solid support.

49. The compound of claim 46 wherein $R^{10}$ is H.

50. The compound of claim 46 wherein p and p' are 0.

51. The compound of claim 46 wherein Y is $NR^2$; $R^2$ is selected independently from H, $CH_3$, $CH_2CH_3$, and $CH(CH_3)_2$; $R^3$ is selected independently from H and $CH_3$; n is selected independently from 1 and 2; m is selected independently from 0 and 1; $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$; and W is O.

52. A compound of Formula XI:

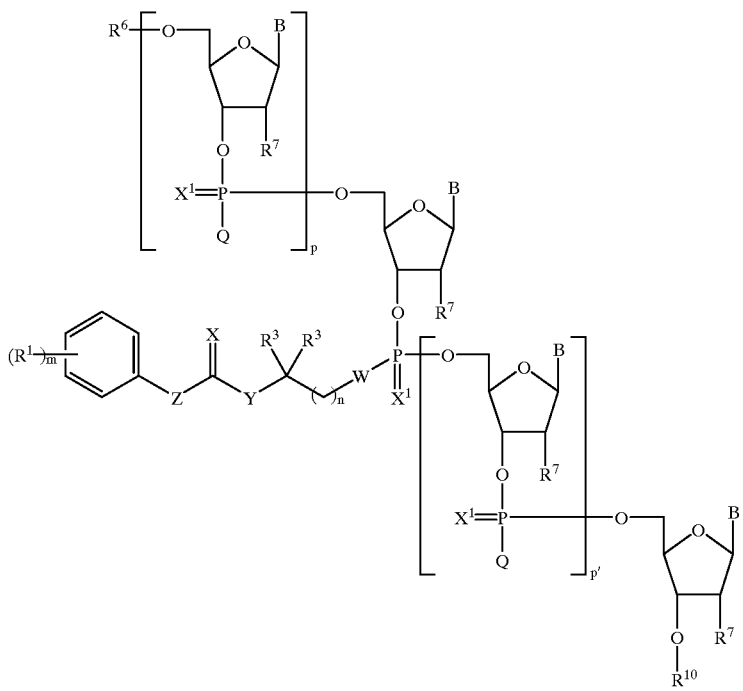

XI wherein:
W is selected independently from O and S;
X is selected independently from O and S;
Y is selected independently from O and $NR^2$;
Z is selected independently from a single bond, O, and $NR^2$;
$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl;
alternatively, two $R^1$ groups, when on adjacent carbons of the phenyl ring, join to form a napthyl ring that includes said phenyl ring;
$R^2$, at each occurrence, is selected independently from H, $C_{1-6}$ alkyl, $C_{2-6}$ alkenyl, $C_{2-6}$ alkynyl, $C_{3-6}$ cycloalkyl, and phenyl;
$R^3$, at each occurrence, is selected independently independently from hydrogen, $C_{1-6}$ alkyl, $C_{2-6}$ alkenyl, $C_{2-6}$ alkynyl, $C_{3-6}$ cycloalkyl, and phenyl;
$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;
$R^6$ is selected independently from H, a hydroxyl protecting group, and a linker connected to a solid support;
$R^7$, at each occurrence, is indepedently H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, dilulfide, silyl, aryl, heterocycle, carbocycle, intercalator, reporter molecule, conjugate, polyamine, polyamide, polyalkylene glycol, polyether, or one of formula XII or XIII:

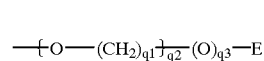

XII

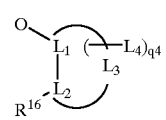

XIII wherein
E is selected from $C_1$–$C_{10}$ alkyl, $N(R^{15})(R^{17})$ and $N=C(R^{15})(R^{17})$;
$R^{15}$ and $R^{17}$ is independently selected from H, $C_1$–$C_{10}$ alkyl, dialkylaminoalkyl, a nitrogen protecting group, a tethered or untethered conjugate group, a linker to a solid support, or alternatively $R^{15}$ and $R^{17}$, together, are joined in a nitrogen protecting group or a ring structure that can include at least one additional heteroatom selected from N and O;

$q^1$ is from 1 to 10;
$q^2$ is from 1 to 10;
$q^3$ is 0 or 1;
$R^{16}$ is $OR^{18}$, $SR^{18}$, or $N(R^{18})_2$;
$R^{18}$ is selected independently from H, $C_1$–$C_8$ alkyl, $C_1$–$C_8$ haloalkyl, $C(=NH)N(H)R^{19}$, $C(=O)N(H)R^{19}$ and $OC(=O)N(H)R^{19}$;
$R^{19}$ is H or $C_1$–$C_8$ alkyl;
$L_1$, $L_2$ and $L_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;
$L_4$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R^{15})(R^{17})$ $OR^{15}$, halo, $SR^{15}$ or CN; and
$q^4$ is, 0, 1 or 2;
$R_8$ is selected independently from $NR^{8a}R^{8b}$, and a 5–6 membered heterocyclic system containing 1–4 heteroatoms selected independently from N, O, and S;
$R^{8a}$ and $R^{8b}$, at each occurrence, are selected independently from $C_{1-10}$ alkyl and $C_{3-7}$ cycloalkyl;
n is selected independently from 0, 1, 2, and 3;
m is selected independently from 0, 1, 2, and 3;
$X^1$ is selected independently from O and S;
B, at each occurrence, is independently selected independently from a protected or unprotected naturally occurring nucleobase, and a protected or unprotected non-naturally occurring nucleobase;
$R^{10}$ is selected independently from H, a hydroxyl protecting group, and a linker connected to a solid support;
Q, at each occurrence, is selected independently from SH, OH, and

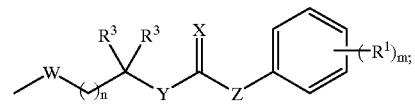

p' is an integer selected independently from 0 to about 50;
p is an integer selected independently from 0 to about 50; with the provisos that the sum of p and p' does not exceed 50, and $R^6$ and $R^{10}$ are not both simultaneously a linker connected to a solid support.

53. The compound of claim 52 wherein $R^{10}$ is a linker connected to a solid support.

54. The compound of claim 52 wherein $R^{10}$ is H.

55. The compound of claim 52 wherein $R^3$ is selected independently from H and $CH_3$; n is selected independently from 1 and 2; m is selected independently from 0 and 1; $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$; and W is O.

56. The compound of claim 52, wherein $R^3$ is selected independently from H and $CH_3$; n is selected independently from 1 and 2; m is selected independently from 0 and 1; $R^1$ is in the meta or para position and is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$; and W is O.

57. The compound of claim 56, wherein $R^3$ is H, Y is $NR^2$, $R^2$ is $CH(CH_3)_2$, X is O, Z is a bond, m is 1, and $R^1$ is $OCH_3$ and is in the para position.

58. The compound of claim 52 wherein each Q has the formula:

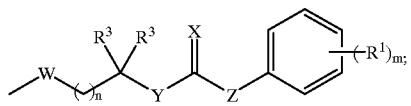

and p is an integer selected independently from 2 to 50.

59. A compound of Formula VI:

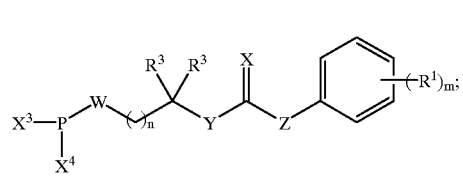

wherein:

W is selected independently from O and S;

X is selected independently from O and S;

Y is selected independently from O and $NR^2$;

Z is selected independently from a single bond, O, and $NR^2$;

$R^1$, at each occurrence, is selected independently from $C_{1-6}$ alkyl, $C_{2-6}$ alkenyl, $C_{2-6}$ alkynyl, $C_{3-6}$ cycloalkyl, CN, $NO_2$, Cl, Br, F, I, $CF_3$, $OR^4$, $NR^{5a}R^{5b}$, and phenyl;

alternatively, two $R^1$ groups, when on adjacent carbons of the phenyl ring, join to form a napthyl ring that includes said phenyl ring;

$R^2$, at each occurrence, is selected independently from H, $C_{1-6}$ alkyl, $C_{2-6}$ alkenyl, $C_{2-6}$ alkynyl, $C_{3-6}$ cycloalkyl, and phenyl;

$R^3$, at each occurrence, is selected independently from hydrogen, $C_{1-6}$ alkyl, $C_{2-6}$ alkenyl, $C_{2-6}$ alkynyl, $C_{3-6}$ cycloalkyl, and phenyl;

$R^4$ is selected independently from $C_{1-6}$ alkyl, $C_{3-6}$ cycloalkyl, and phenyl;

$R^{5a}$ and $R^{5b}$, at each occurrence, are selected independently from $C_{1-6}$ alkyl, $C_{3-6}$ cycloalkyl, and phenyl;

n is selected independently from 0, 1, 2, and 3;

m is selected independently from 0, 1, 2, and 3.

$X^3$ is selected independently from Br, Cl, and I; and $X^4$ is selected independently from $NR^aR^b$, and a 5–6 membered heterocyclic system containing 1–4 heteroatoms selected from N, O, and S;

$R^a$ and $R^b$, at each occurrence, are selected independently from $C_{1-10}$ alkyl and $C_{3-7}$ cycloalkyl.

60. The compound of claim 59 wherein $R^1$ is selected independently from $CH_3$, $CH_2CH_3$, $CH(CH_3)_2$, CN, $NO_2$, $OCH_3$, $OCH_2CH_3$, $OCH(CH_3)_2$, $N(CH_3)_2$, $N(CH_2CH_3)_2$, and $N(CH(CH_3)_2)_2$; $R^2$ is selected independently from H, $CH_3$, $CH_2CH_3$, and $CH(CH_3)_2$; $R^3$ is selected independently from H and $CH_3$; n is selected independently from 1 and 2; and m is selected independently from 0 and 1.

61. The compound of claim 60 wherein $X^3$ is Cl; and $R^a$ and $R^b$ are isopropyl.

* * * * *